(12) United States Patent
Goebbel et al.

(10) Patent No.: US 8,134,018 B2
(45) Date of Patent: Mar. 13, 2012

(54) PROCESS FOR THE EPOXIDATION OF AN OLEFIN WITH IMPROVED ENERGY BALANCE

(75) Inventors: Hans-Georg Goebbel, Kallstadt (DE); Henning Schultz, Mannheim (DE); Peter Schultz, Bad Duerkheim (DE); Renate Patrascu, Stade (DE); Malte Schulz, Hollern-Tw (DE); Meinolf Weidenbach, Drochtersen (DE)

(73) Assignees: BASF SE, Ludwigshafen (DE); The Dow Chemical Company, Midland, MI (US)

( * ) Notice: Subject to any disclaimer, the term of this patent is extended or adjusted under 35 U.S.C. 154(b) by 564 days.

(21) Appl. No.: 11/814,110

(22) PCT Filed: Jan. 9, 2006

(86) PCT No.: PCT/EP2006/050092
§ 371 (c)(1), (2), (4) Date: Jul. 20, 2009

(87) PCT Pub. No.: WO2006/077183
PCT Pub. Date: Jul. 27, 2006

(65) Prior Publication Data
US 2010/0081834 A1    Apr. 1, 2010

Related U.S. Application Data

(63) Continuation-in-part of application No. 11/036,051, filed on Jan. 18, 2005, now abandoned.

(51) Int. Cl.
*C07D 301/12* (2006.01)
(52) U.S. Cl. ....................................................... 549/531
(58) Field of Classification Search .................... 549/531
See application file for complete search history.

(56) References Cited

U.S. PATENT DOCUMENTS

| | | | |
|---|---|---|---|
| 5,397,475 | A | 3/1995 | Millar et al. |
| 5,932,187 | A | 8/1999 | Ledon et al. |
| 6,380,119 | B1 | 4/2002 | Grosch et al. |
| 6,756,503 | B2 | 6/2004 | Teles et al. |
| 6,815,552 | B2 | 11/2004 | Strebelle et al. |
| 2003/0146080 | A1 | 8/2003 | Teles et al. |
| 2005/0240037 | A1 | 10/2005 | Bassler et al. |
| 2005/0258026 | A1 | 11/2005 | Bassler et al. |

FOREIGN PATENT DOCUMENTS

| | | |
|---|---|---|
| DE | 4222109 | 1/1994 |
| EP | 0200260 | 12/1986 |
| EP | 0311983 | 4/1989 |
| EP | 0405978 | 1/1991 |
| EP | 1122249 | 8/2001 |
| EP | 1293505 | 3/2003 |
| WO | WO-98/55228 | 12/1998 |
| WO | WO-02/14298 | 2/2002 |
| WO | WO-03/018567 | 3/2003 |
| WO | WO-2004/009566 | 1/2004 |
| WO | WO-2004/009572 | 1/2004 |
| WO | WO-2004/074268 | 9/2004 |

OTHER PUBLICATIONS

"Hydrogen Peroxide", Ullman's Encyclopedia of Industrial Chemistry, 1989, vol. A 13, pp. 447-457.

*Primary Examiner* — Bernard Dentz
(74) *Attorney, Agent, or Firm* — Oblon, Spivak, McClelland, Maier & Neustadt, L.L.P.

(57) ABSTRACT

The invention relates to a process for the epoxidation of an olefin comprising
(a) reacting the olefin with hydrogen peroxide in the presence of methanol as solvent in at least two reaction stages to obtain a mixture (M-a) comprising olefin oxide, unreacted olefin, methanol and water, wherein between at least two reaction stages, olefin oxide is separated by distillation;
(b) separating unreacted olefin from the mixture (M-a) by distillation to obtain a mixture (M-bi) comprising at least 80 wt.-% of olefin and a mixture (M-bii) comprising methanol, water and at least 7 wt.-% of olefin oxide;
(c) separating olefin oxide from the mixture (M-bii) in at least one distillation stage to obtain a mixture (M-ci) comprising at least 99 wt.-% of olefin oxide and a mixture (M-cii) comprising water and at least 55 wt.-% of methanol;
(d) separating methanol from the mixture (M-cii) in at least one distillation stage to obtain a mixture (M-di) comprising at least 85 wt.-% of methanol and up to 10 wt.-% of water, and a mixture (M-dii) comprising at least 90 wt.-% of water;
wherein a vapor top stream (Td) obtained from at least one distillation column used in (d), said vapor top stream (Td) comprising at least 85 wt.-% methanol, is used to operate at least partially at least one vaporizer used in at least one distillation column used in at least one of stages (a), (b) and (c).

22 Claims, No Drawings

PROCESS FOR THE EPOXIDATION OF AN OLEFIN WITH IMPROVED ENERGY BALANCE

RELATED APPLICATIONS

This application is a national stage application (under 35 U.S.C. §371) of PCT/EP2006/050092 filed Jan. 9, 2006, which claims benefit of U.S. patent application Ser. No. 11/036,051 filed Jan. 18, 2005.

BACKGROUND OF THE INVENTION

Among publications on the subject of the preparation of propylene oxide, there are only a few which are concerned with energy integration aspects.

EP 1 293 505 A1 describes a process for the epoxidation of olefins wherein a product stream from the epoxidation reaction which contains olefin, olefin oxide, water-miscible organic solvent, hydrogen peroxide and water, is separated into an overhead product containing olefin, olefin oxide and organic solvent, and into a bottom product containing organic solvent, hydrogen peroxide and water, whereby 20 to 60% of the total amount of organic solvent is removed with the overhead product, and wherein a pre-evaporator with less than 10 theoretical separation stages is used, the separation being carried out at a pressure of 1.5 to less than 3 bar. As the only vague hint to an energy integration aspect, it is stated that there is a possibility to use an integrated heat management in order to improve energy efficiency. In this context, it is disclosed that said pre-evaporator and an optionally present stripper can be heated with the condensation heat of vapors resulting from subsequent distillation stages. In case methanol is used as solvent, a methanol head product having a higher temperature than the bottom temperature of said pre-evaporator and said stripper can be used to heat the pre-evaporator and the stripper. Thus, EP 1 293 505 A1 restricts the heat management to a very specific process in which a pre-evaporator and a stripper are used as apparatuses in an epoxidation process.

WO 02/14298 A1 describes a continuous process for the preparation of an olefinic oxide by direct oxidation of an olefin with hydrogen peroxide. Among other stages, this process comprises feeding a reaction product comprising unreacted hydrogen peroxide, epoxidation reaction by-products, water and reaction solvent into a decomposition zone to decompose hydrogen peroxide. For this purpose, an aqueous basic solution is additionally fed into the decomposition zone. According to a preferred embodiment, a suspension catalyst is used as epoxidation catalyst. In the context of WO 02/14298 A1, it is disclosed that the condensation heat recovered at the top of a specific distillation zone is used to serve at least some of the boiling needs of the process. Into this distillation zone, two streams are fed, one of which is a liquid phase comprising reaction by-products, water and solvent, the other being obtained from a condensation zone and comprising solvent. As to the stages of the overall process and to any specifics about the amounts of the condensation heat is used, WO 02/14298 A1 is silent.

U.S. Pat. No. 6,756,503 B2 relates to a process for producing propylene oxide which comprises reacting propene with hydrogen peroxide in the presence of methanol thus obtaining a mixture comprising propylene oxide, methanol, water and unreacted hydrogen peroxide, separating therefrom a mixture comprising methanol, water and hydrogen peroxide, and separating therefrom water thus obtaining a mixture comprising methanol and methyl formate. It is disclosed that, in case heat recovery is to be realized, two or more distillation columns are preferred. As to any specifics about heat recovery, this document is silent.

WO 2004/074268 A1 discloses a process for the reaction of an organic compound having at least one C-C double bond with hydrogen peroxide in the presence of at least one catalytically active substance and methanol wherein water is separated from a product stream comprising methanol and water and a resulting product stream comprising methanol and at least 3 wt.-% of water is recycled into the process. It is disclosed that a top stream from a distillation column can be used to directly heat up an evaporator in the epoxidation process or in a different process. In the context of WO 2004/074268 A1, it is described that two distillation columns can be used to separate water from above-mentioned mixture wherein the top fractions of both columns are combined to give a product stream having a water content of at least 3 wt.-%. As to any specifics about the stage or the stages said evaporator is used for, this document is silent.

US 2003/146080 A1 describes a process for the production of propylene oxide in the presence of methanol in which propylene oxide is separated from a mixture comprising propylene oxide and methanol, and in which the resulting mixture is worked up wherein methanol is separated from a mixture comprising methanol and methyl formate. It is disclosed that from a mixture comprising methanol and water, water can be separated wherein two distillation columns can be used. It is explicitly described that other process streams can be heated up with the condensation heat obtained at the top of these columns by cooling the condenser of at least one of said columns with water and using the hot water or the steam resulting from cooling.

WO 2004/009572 A1 describes a process for the continuous distillation of a solvent used for the synthesis of an oxirane in which a mixture comprising solvent and resulting from synthesis and subsequent work up is separated in a dividing wall column, wherein the solvent is taken as medium boiling fraction from the side of the dividing wall column. The dividing wall column can be configured as thermally coupled columns which are spatially separated from each other.

WO 2004/009566 A1 discloses a process for the continuously operated distillation of methanol which is used as solvent in a process for producing propylene oxide. It is disclosed that a solvent mixture is separated in a dividing wall column so that a top fraction comprising methanol, a fraction taken from the side comprising methoxy propanols as an azetrope with water, and a bottoms fraction comprising water and propylene glycol are obtained. The methanol obtained as top fraction can be condensed and recycled into the epoxidation process.

Accordingly, the prior art describes either a mere concept concerning the possibility of heat integration or relates to very specific embodiments of epoxidation processes in which not more than one or two stages of the overall process are involved in the heat integration aspect.

Therefore, it is an object of the present invention to provide a highly integrated process for the production of an olefin oxide in which at least three process stages of the overall process are involved with regard to minimization of energy consumption.

It is a further object of the present invention to provide a highly integrated process for the production of an olefin oxide in which the top vapor stream obtained from the separation of methanol from a product stream of the epoxidation process is used to operate evaporators used in at least three process stages of the overall epoxidation process.

It is another object of the present invention to provide a highly integrated process for the production of propylene oxide in which the top vapor stream obtained from the separation of methanol from a product stream of the propene epoxidation process is used to operate evaporators used in at least three process stages of the overall epoxidation process.

It is still another object of the present invention to provide a highly integrated process for the production of an olefin oxide, preferably propylene oxide, in which not only the top vapor stream obtained from the separation of methanol from a product stream of the propene epoxidation process is used to operate evaporators used in at least three process stages of the overall epoxidation process, but in which at least one suitable additional method is employed rendering the process economically and ecologically still more positive concerning the overall energy balance.

It is yet another object of the present invention to provide a highly integrated process for the production of an olefin oxide, preferably propylene oxide, in which above-mentioned advantages are further combined with an optimized, preferably energetically optimized methanol separation.

SUMMARY OF THE INVENTION

Therefore, the present invention provides a process for the epoxidation of an olefin comprising
(a) reacting the olefin with hydrogen peroxide in the presence of methanol as solvent in at least two reaction stages to obtain a mixture (M-a) comprising olefin oxide, unreacted olefin, methanol and water, wherein between at least two reaction stages, olefin oxide is separated by distillation;
(b) separating unreacted olefin from the mixture (M-a) by distillation to obtain a mixture (M-bi) comprising at least 80 wt.-% of olefin and a mixture (M-bii) comprising methanol, water and at least 7 wt.-% of olefin oxide;
(c) separating olefin oxide from the mixture (M-bii) in at least one distillation stage to obtain a mixture (M-ci) comprising at least 99 wt.-% of olefin oxide and a mixture (M-cii) comprising water and at least 55 wt.-% of methanol;
(d) separating methanol from the mixture (M-cii) in at least one distillation stage to obtain a mixture (M-di) comprising at least 85 wt.-% of methanol and up to 10 wt.-% of water, and a mixture (M-dii) comprising at least 90 wt.-% of water;
wherein a vapor top stream (Td) obtained from at least one distillation column used in (d), said vapor top stream (Td) comprising at least 85 wt.-% methanol, is used to operate at least partially at least one vaporizer used in at least one distillation column used in at least one of stages (a), (b) and (c).

The present invention also provides a process for the epoxidation of propene comprising
(a) reacting propene with hydrogen peroxide in the presence of methanol as solvent in at least two reaction stages to obtain a mixture (M-a) comprising propylene oxide, unreacted propene, methanol and water, wherein between at least two reaction stages, propylene oxide is separated by distillation;
(b) separating unreacted propene from the mixture (M-a) by distillation to obtain a mixture (M-bi) comprising at least 80 wt.-% of propene and a mixture (M-bii) comprising methanol, water and at least 7 wt.-% of propylene oxide;
(c) separating propylene oxide from the mixture (M-bii) in at least one distillation stage to obtain a mixture (M-ci) comprising at least 99 wt.-% of propylene oxide and a mixture (M-cii) comprising water and at least 55 wt.-% of methanol;
(d) separating methanol from the mixture (M-cii) in at least one distillation stage to obtain a mixture (M-di) comprising at least 85 wt.-% of methanol and up to 10 wt.-% of water, and a mixture (M-dii) comprising at least 90 wt.-% of water;
wherein a vapor top stream (Td) obtained from at least one distillation column used in (d), said vapor top stream (Td) comprising at least 85 wt.-% methanol, is used to operate at least partially at least one vaporizer used in at least one distillation column used in at least one of stages (a), (b) and (c).

The present invention also relates to a process for the epoxidation of propene, comprising
(a) reacting the propene with hydrogen peroxide in the presence of methanol as solvent in at least two reaction stages to obtain a mixture (M-a) comprising propylene oxide, unreacted propene, propane, methanol and water, wherein between at least two reaction stages, propylene oxide is separated by distillation;
(b) separating unreacted propene from the mixture (M-a) by distillation to obtain a mixture (M-bi) comprising propane and at least 80 wt.-% of propene, and a mixture (M-bii) comprising methanol, water and at least 7 wt.-% of propylene oxide;
(x) separating propene from the mixture (M-bi) by distillation to obtain a mixture (M-x) comprising at least 95 wt.-% of propene, and re-introducing (M-x) into (a);
(c) separating the propylene oxide from the mixture (M-bii) in at least one distillation stage to obtain a mixture (M-ci) comprising at least 99 wt.-% of propylene oxide and a mixture (M-cii) comprising water, at least one compound having a boiling temperature lower than methanol and lower than water at a given pressure, and at least 60 wt.-% of methanol;
(y) separating the at least one compound having a boiling point lower than methanol and lower than water from the mixture (M-cii) by distillation to obtain a mixture (M-y) comprising from 40 to 80 wt.-% of methanol and from 10 to 55 wt.-% of water;
(d) separating methanol from the mixture (M-y) in at least one distillation stage to obtain a mixture (M-di) comprising at least 85 wt.-% of methanol and up to 10 wt.-% of water, and a mixture (M-dii) comprising at least 90 wt.-% of water, and re-introducing (M-di) into (a);
(e) evaporating the mixture (M-dii),
wherein a vapor top stream (Td) is obtained from at least one distillation column used in (d), said vapor top stream (Td) comprising at least 85 wt.-% methanol, and wherein from 15 to 50 wt.-% of (Td) are used to operate at least partially a vaporizer used in (a), from 2 to 15 wt.-% of (Td) are used to operate at least partially a vaporizer used in (b), from 1 to 10 wt.-% of (Td) are used to operate at least partially a vaporizer used in (x), from 1 to 40 wt.-% of (Td) are used to operate at least partially a vaporizer used in (c), from 15 to 50 wt.-% of (Td) are used to operate at least partially a vaporizer used in (y), and from 10 to 40 wt.-% of (Td) are used to operate at least partially a vaporizer used in (e).

The present invention also relates to a process for the epoxidation of propene, comprising
(a) reacting the propene with hydrogen peroxide in the presence of methanol as solvent in at least two reaction stages to obtain a mixture (M-a) comprising propylene oxide, unreacted propene, propane, methanol and water, between at least two reaction stages, propylene oxide is separated by distillation in a divided wall column, wherein separated methanol is recycled into (a);

(b) separating unreacted propene from the mixture (M-a) by distillation to obtain a mixture (M-bi) comprising propane and at least 80 wt.-% of propene, and a mixture (M-bii) comprising methanol, water and at least 7 wt.-% of propylene oxide;

(x) separating propene from the mixture (M-bi) by distillation to obtain a mixture (M-x) comprising at least 95 wt.-% of propene, and re-introducing (M-x) into (a);

(c) separating the propylene oxide from the mixture (M-bii) in two distillation columns, wherein from the first distillation column, a first mixture comprising at least 99 wt.-% of propylene oxide and a mixture (M-cii) comprising water, at least one compound having a boiling temperature lower than methanol and lower than water at a given pressure, and at least 60 wt.-% of methanol, are obtained, said first mixture being introduced into the second distillation column from which a mixture (M-ci) comprising at least 99.8 wt.-% propylene oxide is obtained;

(y) separating the at least one compound having a boiling point lower than methanol and lower than water from the mixture (M-cii) by distillation to obtain a mixture (M-y) comprising from 40 to 80 wt.-% of methanol and from 10 to 55 wt.-% of water;

(d) separating methanol from the mixture (M-y) wherein
  (i) the mixture (M-y) is introduced into a first distillation column (K1) from which the vapor top stream (Td) is obtained, the distillation in (K1) being carried out at a top pressure of from 2.5 to 6 bar; and
  (ii) the bottoms stream obtained from (K1) is introduced into a second distillation column (K2), the distillation in (K2) being carried out at a top pressure of from 9 to 13 bar, (K2) being a dividing wall column,
  and wherein, prior to introducing into (K2), the bottoms stream obtained from (K1) is heated to a temperature from 130 to 175° C. with the bottoms stream obtained from (K2), and wherein the condenser used to condense the top stream obtained from (K2) is simultaneously used as vaporizer of (K1), and wherein (Td) and the top stream obtained from (K2) are re-introduced into (a);

(e) evaporating the mixture (M-dii), wherein a vapor top stream (Td) obtained from at least one distillation column used in (d), said vapor top stream (Td) comprising at least 85 wt.-% methanol, is used to operate at least partially at least one vaporizer used in at least one distillation column used in at least one of stages (a), (b), (c), (e), (x) and (y).

The present invention also relates to a process for the epoxidation of propene, comprising (a) reacting the propene with hydrogen peroxide in the presence of methanol as solvent in at least two reaction stages to obtain a mixture (M-a) comprising propylene oxide, unreacted propene, propane, methanol and water, wherein between at least two reaction stages, propylene oxide is separated by distillation;

(b) separating unreacted propene from the mixture (M-a) by distillation to obtain a mixture (M-bi) comprising propane and at least 80 wt.-% of propene, and a mixture (M-bii) comprising methanol, water and at least 7 wt.-% of propylene oxide;

(x) separating propene from the mixture (M-bi) by distillation to obtain a mixture (M-x) comprising at least 95 wt.-% of propene, and re-introducing (M-x) into (a);

(c) separating the propylene oxide from the mixture (M-bii) in two distillation columns, wherein from the first distillation column, a first mixture comprising at least 99 wt.-% of propylene oxide and a mixture (M-cii) comprising water, at least one compound having a boiling temperature lower than methanol and lower than water at a given pressure and at least 60 wt.-% of methanol, are obtained, said first mixture being introduced into the second distillation column from which a mixture (M-ci) comprising at least 99.8 wt.-% propylene oxide is obtained;

(y) separating the at least one compound having a boiling point lower than methanol and lower than water from the mixture (M-cii) by distillation to obtain a mixture (M-y) comprising from 40 to 80 wt.-% of methanol and from 10 to 55 wt.-% of water;

(d) separating methanol from the mixture (M-y) wherein
  (i) the mixture (M-y) is introduced into a first distillation column (K1) from which the vapor top stream (Td) is obtained, the distillation in (K1) being carried out at a top pressure of from 2.5 to 6 bar; and
  (ii) the bottoms stream obtained from (K1) is introduced into a second distillation column (K2), the distillation in (K2) being carried out at a top pressure of from 9 to 13 bar, (K2) being a dividing wall column,
  and wherein, prior to introducing into (K2), the bottoms stream obtained from (K1) is heated to a temperature from 140 to 170° C. with the bottoms stream obtained from (K2), and wherein the condenser used to condense the top stream obtained from (K2) is simultaneously used as vaporizer of (K1), and wherein (Td) and the top stream obtained from (K2) are re-introduced into (a);

(e) evaporating the mixture (M-dii), wherein a vapor top stream (Td) is obtained from at least one distillation column used in (d), said vapor top stream (Td) comprising at least 85 wt.-% methanol, wherein from 20 to 40 wt.-% of (Td) are used to operate at least partially a vaporizer used in (a), from 3 to 10 wt.-% of (Td) are used to operate at least partially a vaporizer used in (b), from 3 to 10 wt.-% of (Td) are used to operate at least partially a vaporizer used in (x), from 0 to 10 wt.-% of (Td) are used to operate at least partially a vaporizer used in the first distillation column in (c), from 2 to 20 wt.-% of (Td) are used to operate at least partially a vaporizer used in the second distillation column in (c), from 20 to 40 wt.-% of (Td) are used to operate at least partially a vaporizer used in (y), from 15 to 35 wt.-% of (Td) are used to operate at least partially a vaporizer used in (e), and from 3 to 30 wt.-% of (Td) are used to at least partially operate at least one control heat exchanger used in the process, said process further comprising at least one further integration method selected from the group consisting of (II) heating the feed of the distillation column used in stage (a) with the bottoms stream of this column and the feed of at least one distillation column used in stage (d) with the bottoms stream of this column;

(III) condensing the top stream obtained from at least one distillation column used in stages (a), (b), (x), (c), (y), and (e) in two stages, wherein in the first stage, the condenser is cooled with water having an inlet temperature of from 15 to 40° C. and in the second stage, the condenser is cooled with water having an inlet temperature of from 5 to 20° C., wherein the inlet temperature of the water used in the second stage is lower than the inlet temperature of the water used in the first stage.

DETAILED DESCRIPTION OF THE INVENTION

According to the present invention, the process for the epoxidation of an olefin comprises (a) reacting the olefin with hydrogen peroxide in the presence of methanol as solvent in at least two reaction stages to obtain a mixture (M-a) comprising olefin oxide, unreacted olefin, methanol and water, wherein between at least two reaction stages, olefin oxide is separated by distillation;

(b) separating unreacted olefin from the mixture (M-a) by distillation to obtain a mixture (M-bi) comprising at least 80 wt.-% of olefin and a mixture (M-bii) comprising methanol, water and at least 7 wt.-% of olefin oxide;

(c) separating olefin oxide from the mixture (M-bii) in at least one distillation stage to obtain a mixture (M-ci) comprising at least 99 wt.-% of olefin oxide and a mixture (M-cii) comprising water and at least 55 wt.-% of methanol;

(d) separating methanol from the mixture (M-cii) in at least one distillation stage to obtain a mixture (M-di) comprising at least 85 wt.-% of methanol and up to 10 wt.-% of water, and a mixture (M-dii) comprising at least 90 wt.-% of water;

wherein a vapor top stream (Td) obtained from at least one distillation column used in (d), said vapor top stream (Td) comprising at least 85 wt.-% methanol, is used to operate at least partially at least one vaporizer used in at least one distillation column used in at least one of stages (a), (b) and (c).

Stage (a)

As to the olefin used according to stage (a), there are no specific restrictions. For example, ethene, propylene, 1-butene, 2-butene, isobutene, butadiene, pentenes, piperylene, hexenes, hexadienes, heptenes, octenes, diisobutene, trimethylpentene, nonenes, dodecene, tridecene, tetradecene to eicosene, tripropene and tetrapropene, polybutadienes, polyisobutenes, isoprene, terpenes, geraniol, linalool, linalyl acetate, methylenecyclopropane, cyclopentene, cyclohexene, norbornene, cycloheptene, vinylcyclohexane, vinyloxirane, vinylcyclohexene, styrene, cyclooctene, cyclooctadiene, vinylnorbornene, indene, tetrahydroindene, methylstyrene, dicyclopentadiene, divinylbenzene, cyclododecene, cyclododecatriene, stilbene, diphenylbutadiene, vitamin A, betacarotene, vinylidene fluoride, allyl halides, crotyl chloride, methallyl chloride, dichlorobutene, allyl alcohol, methallyl alcohol, butenols, butenediols, cyclopentenediols, pentenols, octadienols, tridecenols, unsaturated steroids, ethoxyethene, isoeugenol, anethole, unsaturated carboxylic acids such as acrylic acid, methacrylic acid, crotonic acid, maleic acid, vinylacetic acid, unsaturated fatty acids such as oleic acid, linoleic acid, palmitic acid, naturally occurring fats and oils can be reacted with hydrogen peroxide.

Preference is given to using alkenes containing from 2 to 8 carbon atoms. Particular preference is given to reacting ethene, propene and butene. Very particular preference is given to reacting propylene.

Therefore, the present invention relates to a process as described above wherein the olefin employed in stage (a) is propene and the respective olefin oxide is propylene oxide.

According to stage (a) of the process, an olefin is reacted with hydrogen peroxide in the presence of methanol as solvent in at least two reaction stages to obtain a mixture (M-a) which comprises olefin oxide, unreacted olefin, methanol and water. Between at least two of these reaction stages, olefin oxide is separated by distillation. Therefore, the inventive process comprises at least the following sequence of stages (i) to (iii):

(i) reaction of the olefin, preferably propene, with hydrogen peroxide to give a mixture comprising olefin oxide, preferably propylene oxide, and unreacted olefin, (ii) separation of the unreacted olefin from the mixture resulting from stage (i), (iii) reaction of the olefin which has been separated off in stage (ii) with hydrogen peroxide.

Therefore, stage (a) can comprise, in addition to stages (i) and (iii), at least one further reaction stage and, in addition to stage (ii), at least one further separation stage. According to a preferred embodiment, the process stage (a) consists of these three stages.

As to stages (i) and (iii), there are no specific restrictions as to how the reaction is carried out.

Accordingly, it is possible to carry out one of the reactions stages in batch mode or in semi-continuous mode or in continuous mode and independently thereof, the other reaction stage in batch mode or in semi-continuous mode or in continuous mode. According to an even more preferred embodiment, both reaction stages (i) and (iii) are carried out in continuous mode.

The epoxidation reaction in stages (i) and (iii) is preferably carried out in the presence of at least one zeolite catalyst. Zeolites are, as is known, crystalline aluminosilicates having ordered channel and cage structures and containing micropores which are preferably smaller than about 0.9 nm. The network of such zeolites is made up of $SiO_4$ and $AlO_4$ tetrahedra which are joined via shared oxygen bridges. An overview of the known structures may be found, for example, in W. M. Meier, D. H. Olson and Ch. Baerlocher, "Atlas of Zeolite Structure Types", Elsevier, 5th edition, Amsterdam 2001.

Zeolites in which no aluminum is present and in which part of the Si(IV) in the silicate lattice is replaced by titanium as Ti(IV) are also known. These titanium zeolites, in particular those having a crystal structure of the MFI type, and possible ways of preparing them are described, for example, in EP 0 311 983 A2 or EP 0 405 978 A1. Apart from silicon and titanium, such materials can further comprise additional elements such as aluminum, zirconium, tin, iron, cobalt, nickel, gallium, germanium, boron or small amounts of fluorine. In the zeolite catalysts which have preferably been regenerated by the process of the invention, part or all of the titanium of the zeolite can have been replaced by vanadium, zirconium, chromium or niobium or a mixture of two or more thereof. The molar ratio of titanium and/or vanadium, zirconium, chromium or niobium to the sum of silicon and titanium and/or vanadium and/or zirconium and/or chromium and/or niobium is generally in the range from 0.01:1 to 0.1:1.

Titanium zeolites, in particular those having a crystal structure of the MFI type, and possible ways of preparing them are described, for example, in WO 98/55228, EP 0 311 983 A2, EP 0 405 978 A1, EP 0 200 260 A2.

It is known that titanium zeolites having the MFI structure can be identified via a particular X-ray diffraction pattern and also via a lattice vibration band in the infrared (IR) region at about 960 $cm^{-1}$ and thus differ from alkali metal titanates or crystalline and amorphous $TiO_2$ phases.

Specific mention may be made of titanium-, germanium-, tellurium-, vanadium-, chromium-, niobium-, zirconium-containing zeolites having a pentasil zeolite structure, in particular the types which can be assigned X-ray-crystallographically to the structures ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, CDO, CFI, CGF, CGS, CHA, CHI, CLO, CON, CZP, DAC, DDR, DFO, DFT, DOH, DON, EAB, EDI, EMT, EPI, ERI, ESV, ETR, EUO, FAU, FER, FRA, GIS, GIU, GME, GON, GOO, HEU, IFR, ISV, ITE, ITH, ITW, IWR, IWW, JBW, KFI, LAU, LEV, LIO, LOS, LOV, LTA, LTL, LTN, MAR, MAZ, MEI, MEL, MEP, MER, MMFI, MFS, MON, MOR, MSO, MTF, MTN, MTT, MTW, MWW, NAB, NAT, NEES, NON, NPO, OBW, OFF, OSI, OSO, PAR, PAU, PHI, PON, RHO, RON, RRO, RSN, RTE, RTH, RUT, RWR, RWY, SAO, SAS, SAT, SAV, SBE, SBS, SBT, SFE, SFF, SFG, SFH, SFN SFO, SGT, SOD, SSY, STF, STI, STT, TER, THO, TON, TSC, UEI, UFI, UOZ, USI, UTL, VET, VFI VNI, VSV, WEI, WEN, YNU, YUG and ZON,
and also mixed structures of two or more of the abovementioned structures. Furthermore, titanium-containing zeolites having the ITQ-4, SSZ-24, TTM-1, UTD-1, CIT-1 or CIT-5 structure are also conceivable for use in the process of the invention. Further titanium-containing zeolites which may be mentioned are those having the ZSM-48 or ZSM-12 structure.

For the purposes of the present invention, preference is given to using Ti zeolites having an MFI structure, an MEL structure, an MFI/MEL mixed structure or an MWW structure. Further preference is given specifically to the Ti-containing zeolite catalysts which are generally referred to as "TS-1", "TS-2", "TS-3", and also Ti zeolites having a framework structure isomorphous with beta-zeolite. Very particular preference is given to using zeolite catalysts of the TS-1 structure and the Ti-MWW structure.

The catalysts, especially preferably the titanium zeolite catalysts and still more preferably the catalysts having TS1 or MWW structure, can be employed as powder, as granules, as microspheres, as shaped bodies having, for example, the shape of pellets, cylinders, wheels, stars, spheres, honeycombs and so forth, or as extrudates such as extrudates having, for example, a length of from 1 to 10, more preferably of from 1 to 7 and still more preferably of from 1 to 5 mm, and a diameter of from 0.1 to 5, more preferably of from 0.2 to 4 and especially preferably of from 0.5 to 2 mm. In order to increase the bulk density of the extrudates, it is preferred to cut the extrudates with a stream essentially consisting of an inert gas.

For each of these forming methods, it is possible to use at least one additional binder and/or at least one pasting agent and/or at least one pore forming agent. Prior to using the catalyst in the epoxidation reaction of the present invention, it is possible to suitably pretreat the catalyst. In case the catalyst is used as supported catalyst, a carrier can be preferably used which are inert, i.e. which do not react with hydrogen peroxide, olefin, and olefin oxide.

Most preferably, a Ti-TS1 or Ti-MWW catalyst is employed which is produced by first forming microspheres, for example microspheres formed according to EP 0 200 260 A2, and then forming said microspheres to obtain shaped bodies, preferably extrudates as described above.

Therefore, the reactions in stages (i) and (iii) are preferably carried out in suspension or fixed-bed mode, most preferably in fixed-bed mode.

In the inventive process, it is possible to use the same or different types of reactors in stages (i) and (iii). Thus, it is possible to carry out one of the reactions stages in an isothermal or adiabatic reactor and the other reaction stage, independently thereof, in an isothermal or adiabatic reactor. The term "reactor" as used in this respect comprises a single reactor, a cascade of at least two serially connected reactors, at least two reactors which are operated in parallel, or a multitude of reactors wherein at least two reactors are serially coupled and wherein at least two reactors are operated in parallel. According to a preferred embodiment, stage (i) of the present invention is carried out in at least two reactors which are operated in parallel, and stage (iii) of the present invention is carried out in a single reactor. Optionally, stage (iii) can comprise at least one additional reactor which is arranged, for example, as parallel reactor. Preferably, at least one of the additional reactors is operated if, for example, the reactor of stage (iii) is taken out of service for regeneration purposes concerning the catalyst used. According to one embodiment of stage (iii) of the present invention, stage (iii) consists of two reactors arranged as parallel reactors wherein one reactor is used for carrying out the reaction, and wherein in case this reactor has to be taken out of service, for example due to regeneration purposes, the other reactor is taken into service, thus allowing for carrying out the reaction without interruption of the overall process.

Each of the reactors described above, especially the reactors according to the preferred embodiment, can be operated in downflow or in upflow operation mode.

In case the reactors are operated in downflow mode, it is preferred to use fixed-bed reactors which are preferably tubular, multi-tubular or multi-plate reactors, most preferably equipped with at least one cooling jacket. In this case, the epoxidation reaction is carried out at a temperature of from 30 to 80° C., and the temperature profile in the reactors is maintained at a level so that the temperature of the cooling medium in the cooling jackets is at least 40° C. and the maximum temperature in the catalyst bed is 60° C. In case of downflow operation of the reactors, it is possible to chose the reaction conditions such as temperature, pressure, feed rate and relative amounts of starting materials such that the reaction is carried out in a single phase, more preferably in a single liquid phase, or in a multiphase system comprising, for example, 2 or 3 phases. As to the downflow operation mode, it is especially preferred to conduct the epoxidation reaction in a multiphase reaction mixture comprising a liquid aqueous hydrogen peroxide rich phase containing methanol and a liquid organic olefin rich phase, preferably a propene rich phase.

In case the reactors are operated in upflow mode, it is preferred to use fixed-bed reactors. It is still further preferred to use at least two fixed-bed reactors in stage (i) and at least one reactor in stage (iii). According to a still further preferred embodiment, the at least two reactors used in stage (i) are serially connected or operated in parallel, more preferably operated in parallel. Generally, it is necessary to equip at least one of the reactors used in stage (i) and/or (iii) with a cooling means such as a cooling jacket. Especially preferably, at least two reactors are employed in stage (i) which are connected in parallel and can be operated alternately. In case the reactors are operated in upflow mode, the two or more reactors connected in parallel in stage (i) are particularly preferably tube reactors, multi-tube reactors or multi-plate reactors, more preferably multi-tube reactors and especially preferably shell-and-tube reactors comprising a multitude of tubes such as from 1 to 20,000, preferably from 10 to 10,000, more preferably from 100 to 8000, more preferably from 1000 to 7000 and particularly preferably from 3000 to 7000, tubes. To regenerate the catalyst used for the epoxidation reaction, it is possible for at least one of the reactors connected in parallel to be taken out of operation for the respective reaction stage and the catalyst present in this reactor to be regenerated, with at least one reactor always being available for reaction of the starting material or starting materials in every stage during the course of the continuous process.

As cooling medium used for cooling the reaction media in above-mentioned reactors equipped with cooling jackets, there are no specific restrictions. Especially preferred are oils, alcohols, liquid salts or water, such as river water, brackish water and/or sea water, which can in each case, for example, preferably be taken from a river and/or lake and/or sea close to the chemical plant in which the reactor of the invention and the process of the invention are used and, after any necessary suitable removal of suspended material by filtration and/or sedimentation, be used directly without further treatment for cooling the reactors. Secondary cooling water which is preferably conveyed around a closed circuit is particularly useful for cooling purposes. This secondary cooling water is generally essentially deionized or demineralised water to which at least one antifouling agent has preferably been added. More preferably, this secondary cooling water circulates between the reactor of the invention and, for example, a cooling tower. Preference is likewise given to the secondary cooling water being, for example, countercooled in at least one countercurrent heat exchanger by, for example, river water, brackish water and/or sea water.

In stage (iii), particular preference is given to using a shaft reactor, more preferably a continuously operated shaft reactor and particularly preferably a continuously operated, adiabatic shaft reactor.

Therefore, the present invention also relates to a process as described above wherein in stage (i), at least two shell-and-tube reactors each having of from 1 to 20,000 internal tubes and being continuously operated in upflow mode, said reactors being operated in parallel, are employed, and wherein in stage (iii), an adiabatic shaft reactor being being continuously operated in upflow mode, is employed. Still more preferably, the reaction in at least one of these reactors, more preferably in the at least two reactors of stage (i) and still more preferably in all reactors used in states (i) and (iii) is conducted such that in the respective reactor, a single liquid phase is present. Even more preferably, in each of the reactors used in stages (i) and (iii), the catalyst used for the epoxidation reaction is employed as fixed-bed reactor wherein the catalyst is a titanium zeolite catalyst, more preferably a Ti-TS1 or Ti-MWW catalyst and even more preferably a Ti-TS1 catalyst.

The hydrogen peroxide is used in the process according to the invention in the form of an aqueous solution with a hydrogen peroxide content of generally of from 1 to 90 wt.-%, preferably of from 10 to 70 wt.-%, more preferably from 10 to 60 wt.-%. A solution having of from 20 to less than 50 wt.-% of hydrogen peroxide is particularly preferred.

According to another embodiment of the present invention, a crude aqueous hydrogen peroxide solution can be employed. As crude aqueous hydrogen peroxide solution, a solution can be used which is obtained by extraction of a mixture with essentially pure water wherein the mixture results from a process known as anthrachinone process (see, e.g., Ullmann's Encyclopedia of Industrial Chemistry, 5th edition, volume 3 (1989) pages 447-457). In this process, the hydrogen peroxide formed is generally separated by extraction from the working solution. This extraction can be performed with essentially pure water, and the crude aqueous hydrogen peroxide is obtained. According to one embodiment of the present invention, this crude solution can be employed without further purification. The production of such a crude solution is described, for example, in European patent application EP 1 122 249 A1. As to the term "essentially pure water", reference is made to paragraph 10, page 3 of EP 1 122 249 A1 which is incorporated by reference.

To prepare the hydrogen peroxide which is preferably used, it is possible to employ, for example, the anthraquinone process by means of which virtually the entire world production of hydrogen peroxide is produced. An overview of the anthraquinone process is given in "Ullmann's Encyclopedia of Industrial Chemistry", 5th edition, volume 13, pages 447 to 456.

It is likewise conceivable to obtain hydrogen peroxide by converting sulfuric acid into peroxodisulfuric acid by anodic oxidation with simultaneous evolution of hydrogen at the cathode. Hydrolysis of the peroxodisulfuric acid then leads via peroxomonosulfuric acid to hydrogen peroxide and sulfuric acid which is thus obtained back.

Of course, the preparation of hydrogen peroxide from the elements is also possible.

Before hydrogen peroxide is used in the process of the invention, it is possible to free, for example, a commercially available hydrogen peroxide solution of undesirable ions. Conceivable methods are, inter alia, those described, for example, in U.S. Pat. No. 5,932,187, DE 42 22 109 A1 or U.S. Pat. No. 5,397,475. It is likewise possible to remove at least one salt present in the hydrogen peroxide solution from the hydrogen peroxide solution by means of ion exchange in an apparatus which contains at least one nonacidic ion exchanger bed having a flow cross-sectional area F and a height H which are such that the height H of the ion exchanger bed is less than or equal to $2.5 \cdot F^{1/2}$, in particular less than or equal to $1.5 \cdot F^{1/2}$. For the purposes of the present invention, it is in principle possible to use all nonacidic ion exchanger beds comprising cation exchangers and/or anion exchangers. It is also possible for cation and anion exchangers to be used as mixed beds within one ion exchanger bed. In a preferred embodiment of the present invention, only one type of nonacidic ion exchangers is used. Further preference is given to the use of basic ion exchange, particularly preferably that of a basic anion exchanger and more particularly preferably that of a weakly basic anion exchanger.

The reaction in the reactors according to stage (i) is preferably carried out at reaction conditions such that the hydrogen peroxide conversion is at least 80%, more preferably at least 85% and still more preferably at least 90%. The pressure in the reactors is generally in the range of from 10 to 30 bar, more preferably from 15 to 25 bar. The temperature of the cooling water is in the range of preferably from 20 to 70° C., more preferably from 25 to 65° C. and particularly preferably from 30 to 60° C.

According to the preferred embodiment of the invention according to which the reactor or the reactors in stage (i) are fixed-bed reactors, the product mixture obtained therefrom essentially consists of olefin oxide, preferably propylene oxide, unreacted olefin, preferably propene, methanol, water, and hydrogen peroxide.

According to a preferred embodiment, the product mixture obtained from stage (i) has a methanol content in the range of from 55 to 75 wt.-%, especially preferably of from 60 to 70 wt.-%, based on the total weight of the product mixture, a water content in the range of from 5 to 25 wt.-%, especially preferably of from 10 to 20 wt.-%, based on the total weight of the product mixture, an olefin oxide content in the range of from 5 to 20 wt.-%, especially preferably of from 8 to 15 wt.-%, based on the total weight of the product mixture, and an olefin content in the range of from 1 to 10 wt.-%, especially preferably of from 1 to 5 wt.-%, based on the total weight of the product mixture.

The temperature of the product mixture obtained from stage (i) is preferably in the range of from 40 to 60° C., more preferably of from 45 to 55° C. Prior to being fed to the distillation column of (ii), the product mixture is preferably heated up in at least one heat exchanger to a temperature in the range of from 50 to 80° C., more preferably of from 60 to 70° C.

According to an object of the present invention, heating up the product stream obtained from stage (i) is carried out using, at least partially, the bottoms stream of the distillation column of stage (ii). Thus, heat integration of the overall epoxidation process is still further improved. According to a preferred embodiment, of from 50 to 100%, more preferably of from 80 to 100% and especially preferably of from 90 to 100% of the bottoms stream obtained from the distillation column used in (ii) are used for heating up the product stream obtained from (i) from a temperature in the range of from 45 to 55° C. to a temperature in the range of from 65 to 70° C.

According to stage (ii), unreacted olefin is separated from the mixture resulting from stage (i). This separation is carried out by distillation using at least one distillation column. The reaction mixture obtained from the at least one reactor, preferably from the at least two reactors used in stage (i), comprising unreacted olefin, olefin oxide, methanol, water and unreacted hydrogen peroxide, is introduced in the distillation column. The distillation column is preferably operated at a top pressure of from 1 to 10 bar, more preferably of from 1 to 5 bar, more preferably of from 1 to 3 bar and still more preferably of from 1 to 2 bar such as 1, 1.1, 1.2, 1.3, 1.4, 1.5, 1.6, 1.7, 1.8, 1.9 or 2 bar. According to an especially preferred embodiment, the distillation column has from 5 to 60, preferably from 10 to 50 and especially preferably from 15 to 40 theoretical stages.

According to a still further preferred embodiment, the reaction mixture obtained from (i) is fed to the distillation column of (ii) from 2 to 30 theoretical stages below the top, preferably from 10 to 20 theoretical stages below the top of the column.

At the top of the distillation column of (ii), a stream essentially consisting of olefin oxide, preferably propylene oxide, methanol and unreacted olefin, preferably propene, is obtained. At the top of the column, a mixture is obtained having a water content of not more than 0.5 wt.-%, preferably of not more than 0.4 wt.-% and still more preferably of not more than 0.3 wt.-%, and having a hydrogen peroxide content of not more than 100 ppm, preferably of not more than 20 ppm and still more preferably of not more than 10 ppm, in each case based on the total weight of the mixture obtained at the top of the column.

At the bottom of the distillation column, a stream essentially consisting of methanol, water and unreacted hydrogen peroxide is obtained. At the bottom of the column, a mixture is obtained having an olefin, preferably a propene content of not more than 50 ppm, preferably of not more than 10 ppm and still more preferably of not more than 5 ppm, and having a olefin oxide, preferably a propylene oxide content of not more than 50 ppm, preferably of not more than 20 ppm and still more preferably of not more than 10 ppm, in each case based on the total weight of the mixture obtained at the bottom of the column.

Therefore, depending on the respective point of view, distillative separation according to stage (ii) can be described as separation of unreacted olefin or, alternatively, as separation of olefin oxide.

The evaporator of the distillation column used in stage (ii) is at least partially operated using at least partially the top stream (Td). Preferably, from 5 to 60%, more preferably from 15 to 50 and especially preferably from 20 to 40% of (Td) are used to operate the evaporator of the distillation column of stage (ii).

According to a still further preferred embodiment, the distillation column used in (ii) is configured as dividing wall column having at least one side-offtake, preferably one side-offtake. Preferably, the dividing wall column preferably has from 20 to 60, more preferably from 30 to 50 theoretical stages.

The upper combined region of the inflow and offtake part of the dividing wall column preferably has from 5 to 50%, more preferably from 15 to 30%, of the total number of theoretical stages in the column, the enrichment section of the inflow part preferably has from 5 to 50%, more preferably from 15 to 30%, the stripping section of the inflow part preferably has from 15 to 70%, more preferably from 20 to 60%, the stripping section of the offtake part preferably has from 5 to 50%, more preferably from 15 to 30%, the enrichment section of the offtake part preferably has from 15 to 70%, more preferably from 20 to 60%, and the lower combined region of the inflow and offtake part of the column preferably has from 5 to 50%, more preferably from 15 to 30%, in each case of the total number of theoretical stages in the column.

It is likewise advantageous for the inlet via which the product mixture obtained from (i) is fed into the column and the side offtake via which a part of the methanol, preferably of from 0 to 50%, more preferably of from 1 to 40%, still more preferably of from 5 to 30% and especially preferably of from 10 to 25% of the methanol, is taken off as intermediate boiler and, still more preferably, directly fed back to stage (i), to be arranged at different heights in the column relative to the position of the theoretical stages. The inlet is preferably located at a position which is from 1 to 25, more preferably from 5 to 15 theoretical stages above or below the side offtake.

The dividing wall column used in the process of the present invention is preferably configured either as a packed column containing random packing or ordered packing or as a tray column. For example, it is possible to use sheet metal or mesh packing having a specific surface area of from 100 to 1000 $m^2/m^3$, preferably from about 250 to 750 $m^2/m^3$, as ordered packing. Such packing provides a high separation efficiency combined with a low pressure drop per theoretical stage.

In the abovementioned configuration of the column, the region of the column divided by the dividing wall, which consists of the enrichment section of the inflow part, the stripping section of the offtake part, the stripping section of the inflow part and the enrichment section of the offtake part, or parts thereof is/are provided with ordered packing or random packing. The dividing wall can be thermally insulated in these regions.

The differential pressure over the dividing wall column can be utilized as regulating parameter for the heating power. The distillation is advantageously carried out at a pressure at the top of from 1 to 10 bar, preferably from 1 to 5 bar, more preferably from 1 to 3 bar and still more preferably of from 1 to 2 bar such as 1, 1.1, 1.2, 1.3, 1.4, 1.5, 1.6, 1.7, 1.8, 1.9 or 2 bar.

Accordingly, the heating power of the vaporizer at the bottom of the column is selected so as to maintain this pressure range. Consequently, the amount of (Td) used for operating the vaporizer, being preferably from 5 to 60%, more preferably from 15 to 50 and especially preferably from 20 to 40% of the total amount of (Td), can be adapted to comply with the differential pressure to be obtained.

The distillation is then preferably carried out in a temperature range from 65 to 100° C., more preferably from 70 to 85° C. The distillation temperature is measured at the bottom of the tower.

In case such a divided wall column is used, at the top of the distillation column of (ii), a stream essentially consisting of olefin oxide, preferably propylene oxide, methanol and unreacted olefin, preferably propene, is obtained. At the top of the column, a mixture is obtained having a water content of not more than 500 ppm, preferably of not more than 400 ppm, and still more preferably of not more than 300 ppm, and having a hydrogen peroxide content of not more than 50 ppm, preferably of not more than 20 ppm and still more preferably of not more than 10 ppm, in each case based on the total weight of the mixture obtained at the top of the column. Furthermore, the top stream obtained has an olefin, preferably a propene content of from 15 to 35 wt.-%, preferably of from 20 to 30 wt.-% and still more preferably of from 20 to 25 wt.-%, an olefin oxide, preferably a propylene oxide content of from 50 to 80 wt.-%, preferably of from 55 to 75 wt.-% and especially preferably of from 60 to 70 wt.-%, and a methanol content of from 5 to 20 wt.-%, more preferably of from 7.5 to 17.5 wt.-% and especially preferably of from 10 to 15 wt.-%, in each case based on the total weight of the top stream.

At the side-offtake of the distillation column, a stream essentially consisting of methanol and water is obtained. At the side-offtake of the column, a mixture is obtained having a methanol content of at least 95 wt.-%, preferably at least 96 wt.-% and still more preferably at least 97 wt.-%, and having a water content of not more than 5 wt.-%, preferably of not more than 3.5 wt.-% and still more preferably of not more than 2 wt.-%, in each case based on the total weight of the mixture obtained at the side-offtake of the column.

At the bottom of the distillation column, a stream essentially consisting of methanol, water and unreacted hydrogen peroxide is obtained. At the bottom of the column, a mixture is obtained having an olefin, preferably a propene content of not more than 50 ppm, preferably of not more than 10 ppm and still more preferably of not more than 5 ppm, and having a olefin oxide, preferably a propylene oxide content of not more than 50 ppm, preferably of not more than 20 ppm and still more preferably of not more than 10 ppm, in each case based on the total weight of the mixture obtained at the bottom of the column.

At least part of the stream taken from the side of the dividing wall column can be recycled as solvent into stage (1) of the inventive process. Preferably, at least 90%, more preferably at least 95% of the stream taken from the side-offtake are recycled into stage (i).

The bottoms stream taken from the distillation column, preferably the dividing wall distillation column, essentially consisting of methanol, water and unreacted hydrogen peroxide, is then fed to the reactor of stage (iii). Preferably, the bottoms stream is cooled prior to being introduced into the reactor via, for example, one-stage cooling or two-stage cooling, more preferably to a temperature of from 20 to 40° C., still more preferably to a temperature of from 30 to 40° C. Still more preferably, fresh olefin, preferably propene, is additionally added directly into the reactor of stage (iii) or added to the bottoms stream obtained from (ii) prior to introducing same into the reactor of stage (iii). Alternatively or additionally, fresh hydrogen peroxide can be added.

The selectivity of this reaction in stage (iii) in respect of hydrogen peroxide is preferably in the range from 64 to 99%, more preferably in the range from 72 to 90% and particularly preferably in the range from 75 to 87%.

The selectivity of the overall process with stages (i) to (iii) in respect of hydrogen peroxide is preferably in the range from 78 to 99%, more preferably in the range from 88 to 97% and particularly preferably in the range from 90 to 96%.

The total hydrogen peroxide conversion is preferably at least 99.5%, more preferably at least 99.6%, more preferably at least 99.7% and particularly preferably at least 99.8%.

The reaction mixture obtained from stage (iii) preferably has a methanol content of from 50 to 90 wt.-%, more preferably of from 60 to 85 wt.-% and especially preferably of from 70 to 80 wt.-%, based on the total weight of the reaction mixture. The water content is preferably in the range of from 5 to 45 wt.-%, more preferably of from 10 to 35 wt.-% and especially preferably of from 15 to 25 wt.-%, based on the total weight of the reaction mixture. The olefin oxide, preferably the propylene oxide content, is preferably in the range of from 1 to 5 wt.-%, more preferably of from 1 to 4 wt.-% and especially preferably of from 1 to 3 wt.-%, based on the total weight of the reaction mixture. The olefin, preferably the propene content is preferably in the range of from 0 to 5 wt.-%, more preferably of from 0 to 3 wt.-% and especially preferably of from 0 to 1 wt.-%, based on the total weight of the reaction mixture.

The product mixture taken from the reactor of stage (iii) can be fed as mixture (M-a) into stage (b) of the inventive process. Additionally, the stream taken from the top of the distillation column of stage (ii) ca be combined with the product mixture taken from the reactor of stage (iii) to give mixture (M-a) which is then fed into stage (b) of the inventive process. Alternatively, it is possible to separately feed the product mixture taken from the reactor of stage (iii) and the top stream of the distillation column of stage (ii) into stage (b), the latter embodiment wherein both streams are regarded as constituting mixture (M-a) being preferred.

Stage (b)

According to stage (b), unreacted olefin is separated from the mixture (M-a) by distillation to obtain a mixture (M-bi) comprising at least 80 wt.-% of olefin and a mixture (M-bii) comprising methanol, water and at least 7 wt.-% of olefin oxide.

Separation according to stage (b) is preferably carried out in at least one distillation column, more preferably in one distillation column. Preferably, this column has of from 5 to 40, more preferably of from 10 to 35 and especially preferably of from 15 to 30 theoretical stages.

The distillation column is preferably operated at a top pressure of from 1 to 5 bar, more preferably of from 1 to 4 bar, more preferably of from 1 to 3 bar and still more preferably of from 1 to 2 bar such as 1, 1.1, 1.2, 1.3, 1.4, 1.5, 1.6, 1.7, 1.8, 1.9 or 2 bar.

According to a still further preferred embodiment, a mixture (M-bi) is obtained at the top of the distillation column comprising at least 85 wt.-% of olefin, still more preferably of from 85 to 90 wt.-% of olefin, preferably of propene.

In the context of the present invention, it is possible to introduce propene as chemical grade propene in which propane is present in a volume ratio of propylene to propane of from about 97:3 to about 95:5. In case chemical grade propene is used, the mixture (M-bi) can additionally comprise up to 15 wt.-%, preferably of from 5 to 10 wt.-% of propane, based on the total weight of mixture (M-bi).

Preferably, the mixture (M-bii) obtained as bottoms stream comprises of from 55 to 80 wt.-%, more preferably from 60 to 75 wt.-% and especially preferably from 65 to 70 wt.-% of methanol, of from 13 to 25 wt.-%, more preferably from 15 to 20 wt.-% of water, and at least 7 wt.-%, more preferably at least 8 wt.-%, more preferably at least 9 wt.-% and especially preferably at least 10 wt.-%, for example from 10 to 15 wt.-% such as about 10, about 11, about 12, about 13, about 14 or about 15 wt.-% of olefin oxide, preferably propylene oxide.

The evaporator of the distillation column used in stage (b) of the inventive process is at least partially operated with at least a part of (Td). More preferably, 1 to 20 wt.-% of (Td), more preferably from 2 to 15 wt.-% of (Td) and especially preferably from 3 to 10 wt.-% of (Td) are used to operate the evaporator used in stage (b).

If necessary, at least one feed stream fed into stage (b) can be heated with the bottoms stream obtained from the column used in stage (b).

Stage (c)

According to stage (c), mixture (M-bii) obtained from stage (b) as bottoms stream is subjected to a further distillative separation process in which a mixture (M-ci) comprising at least 99 wt.-% of olefin oxide and a mixture (M-cii) comprising water and at least 55 wt.-% of methanol are obtained.

Separation according to stage (c) is preferably carried out in at least one distillation column, more preferably in one distillation column. Preferably, this column has of from 30 to 110, more preferably of from 40 to 100 and especially preferably of from 50 to 90 theoretical stages.

The distillation column is preferably operated at a top pressure of from 1 bar or less. Especially preferably, the distillation column is operated as a vacuum column at a top pressure of less than 1 bar, more preferably at not more than 0.9 bar, more preferably at not more than 0.8 bar, more preferably at not more than 0.7 bar, and still more preferably at not more than 0.6 bar. Preferred ranges of the top pressure are, for example, from 0.3 to 0.9 bar, more preferably from 0.4 bar to 0.8 bar. Preferred top pressures are, for example, about 0.4 bar or about 0.5 bar or about 0.6 bar or about 0.7 bar or about 0.8 bar.

According to a preferred embodiment of the inventive process, the mixture (M-ci) obtained as top stream comprises at least 99.1 wt.-%, more preferably at least 99.2 wt.-%, more preferably at least 99.3 wt.-%, more preferably at least 99.4 wt.-%, and still more preferably at least 99.5 wt.-% of olefin oxide, preferably propylene oxide. Preferred contents of (M-ci) with respect to olefin oxide are, for example, in the range of from 99.1 to 99.9, more preferably from 99.2 to 99.9, more preferably from 99.3 to 99.9, more preferably from 99.4 to 99.9 and still more preferably from 99.5 to 99.9 wt.-%, based on the total weight of mixture (M-ci).

According to a preferred embodiment of the inventive process, the mixture (M-cii) obtained as bottoms stream comprises of from 55 to 85 wt.-%, more preferably from 65 to 80 wt.-% and especially preferably from 75 to 80 wt.-% of methanol, and of from 15 to 45 wt.-%, more preferably from 20 to 35 wt.-% and especially preferably of from 20 to 25 wt.-% of water, wherein the content of mixture (M-cii) regarding methanol as well as water is higher than the respective content of mixture (M-bii).

The evaporator of the distillation column used in stage (c) of the inventive process is at least partially operated with at least a part of (Td). More preferably, 1 to 50 wt.-% of (Td), more preferably from 1 to 40 wt.-% of (Td) and especially preferably from 2 to 30 wt.-% of (Td) are used to operate the evaporator used in stage (c).

In order to further improve the energy balance of the overall process, the present invention also provides an additional possibility of heat integration. According to this possibility, the top stream obtained from the distillation column of stage (c) having a pressure in the above-mentioned ranges, especially preferably in the range of from 0.4 to 0.8 bar, and temperature in the range of from 10 to 40° C., preferably from 10 to 30° C. and especially preferably from 10 to 20° C., is compressed to obtain a stream having a preferred pressure in the range of from 1 to 10 bar, more preferably from 1 to 5 bar and especially preferably from 2 to 5 bar and a temperature of up to 100° C., more preferably in the range of from 80 to 100° C. The compressed stream obtained is then at least partially used to partially operate the evaporator of the distillation column used in stage (c). Preferably, from 50 to 100% of the top stream, still more preferably from 80 to 95% of the top stream are used to partially operate the evaporator of the distillation column used in stage (c).

According to a further embodiment of the present invention, preferably from 1 to 50 wt.-% of (Td), more preferably from 1 to 40 wt.-% of (Td) and especially preferably from 2 to 30 wt.-% of (Td) are specifically used to start the operation of the evaporator of the distillation column of stage (c), and preferably from 50 to 100% of the top stream, still more preferably from 80 to 95% of the top stream are used to completely operate the evaporator of the distillation column used in stage (c) once the distillation column fully operates. Therefore, (Td) is partially used to start the operation of the evaporator, and the compressed top stream obtained from stage (c) takes over operation of the evaporator.

Thus, in addition to a part of (Td), the top stream obtained from the distillation column of stage (c) is used to operate this distillation column.

According to a further embodiment of the present invention, separation of olefin oxide, preferably propylene oxide, in stage (c) is performed in at least two, more preferably in two distillation columns.

Therefore, the present invention also relates to a process as described above, wherein in (c), the olefin oxide is separated in two distillation columns, and wherein from 0 to 20 wt.-% of (Td) are used to at least partially operate a vaporizer of the first distillation column from which a mixture comprising at least 98 wt.-% of olefin oxide is obtained, said mixture being introduced into the second distillation column, and from 1 to 30 wt.-% of (Td) are used to at least partially operate a vaporizer of the second distillation column from which an olefin oxide stream comprising at least 99.8 wt.-% olefin oxide is obtained.

Still more preferably, the olefin oxide stream obtained from the second distillation column comprises at least 99.9 wt.-% of olefin oxide, still more preferably at least 99.99 wt-% of olefin oxide.

Preferably, the first column has of from 30 to 110, more preferably of from 40 to 100 and especially preferably of from 50 to 90 theoretical stages.

The first column is preferably operated at a top pressure of from 1 bar or less. Especially preferably, the distillation column is operated as a vacuum column at a top pressure of less than 1 bar, more preferably at not more than 0.9 bar, more preferably at not more than 0.8 bar, more preferably at not more than 0.7 bar, and still more preferably at not more than 0.6 bar. Preferred ranges of the top pressure are, for example, from 0.3 to 0.9 bar, more preferably from 0.4 bar to 0.8 bar. Preferred top pressures are, for example, about 0.4 bar or about 0.5 bar or about 0.6 bar or about 0.7 bar or about 0.8 bar.

Preferably, the second column has of from 25 to 60, more preferably of from 30 to 55 and especially preferably of from 35 to 50 theoretical stages.

The second column is preferably operated at a top pressure of from 1 to 7 bar, more preferably from 2 to 6 bar and especially preferably from 3 to 5 bar.

The mixture obtained from the top of the first column which is fed as feed stream to the second column can further contain certain by-products resulting from one or more stages of the overall epoxidation process, having boiling points lower than the olefin oxide, preferably the propylene oxide. Examples for such by-products are aldehydes such as, for example, acetaldehyde and/or formaldehyde. These by-products can be contained in the top stream of the first column in an amount of up to 0.3 wt.-%, preferably up to 0.20 wt.-% and especially preferably up to 0.15 wt.-%, based on the total weight of (M-cii) and referring to the sum of the respective weights of these low-boiling compounds.

It was surprisingly found that choosing a distillation top pressure of this range allows for obtaining a ultrahigh degree of purity of the olefin oxide, preferably propylene oxide, with regard to the low boiling compounds, and simultaneously using at least partially, further preferably exclusively (Td) to operate the vaporizer of the second distillation column of stage (c).

In case two distillation columns are used in stage (c), from 0 to 20 wt.-% of (Td) are used to operate the vaporizer of the first column and from 1 to 30 wt.-% of (Td) are used to operate the vaporizer of the second column. More preferably, from 0 to 15 wt.-% of (Td) are used to operate the vaporizer of the first column and from 1 to 25 wt.-% of (Td) are used to operate the vaporizer of the second column. Especially preferably, from 0 to 10 wt.-% of (Td) are used to operate the vaporizer of the first column and from 2 to 20 wt.-% of (Td) are used to operate the vaporizer of the second column.

If necessary, at least one feed stream fed into at least one distillation column used in stage (c) can be heated with the bottoms stream obtained from this column.

Stage (d)

According to stage (d), mixture (M-cii) obtained from stage (c) as bottoms stream is subjected to a further distillative separation process in which a mixture (M-di) comprising at least 85 wt.-% of methanol and up to 10 wt.-% of water, and a mixture (M-dii) comprising at least 90 wt.-% of water are obtained.

Distillation in stage (d) can be performed in one, two, three or more distillation columns.

According to one aspect of the present invention, distillation in stage (d) is carried out in one distillation column. Preferably, this distillation column has of from 10 to 100, more preferably of from 20 to 90 and especially preferably of from 30 to 70 theoretical stages.

The distillation column is operated at a pressure preferably of from 1 to 12 bar, more preferably of from 2 to 11 bar and especially preferably of from 3 to 10 bar.

The mixture (M-di) obtained from the top of the column comprises at least 85 wt.-% of methanol and up to 10 wt.-% of water, more preferably at least 90 wt.-% of methanol and up to 10 wt.-% of water, more preferably at least 95 wt.-% of methanol and up to 5 wt.-% of water, more preferably at least 96 wt.-% of methanol and up to 4 wt.-% of water and especially preferably at least 97 wt.-% of methanol and up to 3 wt.-% of water.

The reflux ratio of this column is preferably in the range of 1 to 10, more preferably in the range of 2 to 8.

According to a preferred embodiment of the present invention, distillation in stage (d) is performed in a two-pressure distillation process, where in a first distillation column (K1), distillation is carried out at a top pressure which is different from the top pressure of a second distillation column (K2).

According to a still further preferred embodiment of the present invention, the columns (K1) and (K2) are thermally coupled. According to one embodiment, the condenser used to condense the top stream of the first or second distillation column is used simultaneously as the vaporizer of the second or first distillation column. Preferably, the condenser used to condense the top stream obtained from the second distillation column is used simultaneously as the vaporizer of the first distillation column. According to another embodiment, the bottoms stream obtained from column (K1) which is fed as input stream into column (K2) is heated, prior to being introduced into (K2), with the bottoms stream obtained from column (K2). According to a preferred embodiment, these thermal coupling possibilities are combined.

Therefore, the present invention also relates to a process as described above, wherein in stage (d), a two-pressure distillation is performed and the condenser used to condense the top stream obtained from the second distillation column (K2) is used simultaneously as the vaporizer of the first distillation column (K1) and wherein the bottoms stream obtained from column (K1) which is fed as input stream into column (K2) is heated, prior to being introduced into (K2), with the bottoms stream obtained from column (K2).

The term "first column (K1)" as used in the context of the present invention relates to the column into which the mixture (M-cii) is fed. The term "second column (K2)" as used in the context of the present invention relates to the column into which the bottoms stream obtained from (K1) is fed.

The distillation in the first column (K1) is preferably carried out at a top pressure in the range of from 2 to 8 bar, more preferably of from 2 to 6 bar and especially preferably in the range of from 2.5 to 6 bar. The distillation in the second column (K2) is preferably carried out at a top pressure in the range from 8 to 15 bar, more preferably of from 8.5 to 14 bar, and especially preferably in the range from 9 to 13 bar.

Therefore, the present invention also relates to a process as described above, wherein the top pressure of the first distillation column is from 2 to 8 bar and the top pressure of the second distillation column is from 8 to 14 bar.

Therefore, the present invention also relates to a process as described above, wherein in (d), (i) the mixture (M-cii) is introduced into a first distillation column (K1) from which the vapor top stream (Td) is obtained, the distillation in (K1) being carried out at a top pressure of from 2.5 to 6 bar; and (ii) the bottoms stream obtained from (K1) is introduced into a second distillation column (K2), the distillation in (K2) being carried out at a top pressure of from 9 to 13 bar, wherein prior to introducing into (K2), the bottoms stream obtained from (K1) is heated to a temperature from 100 to 180° C. with the bottoms stream obtained from (K2), and wherein the condenser used to condense the top stream obtained from (K2) is simultaneously used as vaporizer of (K1).

Preferably, the bottoms stream obtained from (K1) is heated to a temperature from 110 to 180° C., more preferably from 120 to 180° C., more preferably from 130 to 175° C. and still more preferably from 140 to 170° C.

The reflux ratio of column (K2) is preferably in the range of from 1 to 5, more preferably of from 2 to 4. The reflux ratio is defined as the mass flow of the top stream obtained from column (K2) divided by the mass flow of the fraction of this stream fed back to the top of (K2).

Distillation column (K1) has preferably of from 5 to 30, more preferably from 7 to 25 and especially preferably of from 10 to 20 theoretical stages.

Distillation column (K2) has preferably of from 5 to 60, more preferably from 10 to 55 and especially preferably of from 15 to 50 theoretical stages.

According to a still further preferred embodiment, the distillation column (K2) is configured as dividing wall column having at least one side-offtake, preferably one side-offtake. Preferably, the dividing wall column preferably has from 10 to 60, more preferably from 15 to 50 theoretical stages.

The upper combined region of the inflow and offtake part of the dividing wall column preferably has from 10 to 70%, more preferably from 15 to 55%, the enrichment section of the inflow part preferably has from 5 to 50%, more preferably from 15 to 30%, the stripping section of the inflow part preferably has from 5 to 50%, more preferably from 15 to 30%, the stripping section of the offtake part preferably has from 5 to 50%, more preferably from 15 to 30%, the enrichment section of the offtake part preferably has from 5 to 50%, more preferably from 15 to 30%, and the lower combined region of the inflow and offtake part of the column preferably has from 5 to 50%, more preferably from 15 to 30%, in each case of the total number of theoretical stages in the column.

The dividing wall column (K2) used in the process of the present invention is preferably configured either as a packed column containing random packing or ordered packing or as a tray column. For example, it is possible to use sheet metal or mesh packing having a specific surface area of from 100 to 1000 m$^2$/m$^3$, preferably from about 250 to 750 m$^2$/m$^3$, as ordered packing. Such packing provides a high separation efficiency combined with a low pressure drop per theoretical stage.

In the abovementioned configuration of the column, the region of the column divided by the dividing wall, which consists of the enrichment section of the inflow part, the stripping section of the offtake part, the stripping section of the inflow part and the enrichment section of the offtake part, or parts thereof is/are provided with ordered packing or random packing. The dividing wall can be thermally insulated in these regions.

Compared to a conventional distillation column, the dividing wall column used in stage (d) has the advantage that certain by-products resulting from one or more stages of the overall epoxidation process can be easily separated from methanol. Since mixture (M-di) is most preferably fed back as solvent into stage (a), it was found that using dividing wall columns prevents these by-products from exceeding undesirable concentrations in the methanol loop. Examples for such by-products are compounds such as glycol ethers.

Therefore, the present invention is characterized in that it encompasses, in specific reaction stages, i.e. stages (a) and (d), two dividing wall columns, thus rendering the overall epoxidation process still more effective.

Therefore, the present invention also relates to a process as described above wherein column (K2) is a dividing wall column.

In case stage (d) is performed as two-pressure distillation using a conventional distillation column (K1) and a dividing wall column (K2), the top stream (Td) obtained from the top of column (K1) comprises at least 85 wt.-% of methanol and up to 10 wt.-% of water, more preferably at least 90 wt.-% of methanol and up to 10 wt.-% of water, more preferably at least 95 wt.-% of methanol and up to 5 wt.-% of water, more preferably at least 96 wt.-% of methanol and up to 4 wt.-% of water and especially preferably at least 97 wt.-% of methanol and up to 3 wt.-% of water. According to particularly preferred embodiment, the top stream (Td) comprises less than 3 wt.-% of water such as, for example, from 1 to 2 wt.-% of water.

The temperature of (Td) is preferably in the range of from 90 to 130° C., more preferably of from 95 to 120° C. and especially preferably of from 100 to 110° C.

The bottoms stream obtained from (K1) has a preferred temperature of from 100 to 140° C., more preferably in the range of from 110 to 130° C. According to the above-described preferred embodiment, this bottoms stream is fed into (K2) and, prior to feeding, heated with the bottoms stream of (K2) to a temperature of from 110 to 180° C., more preferably from 120 to 180° C., more preferably from 130 to 175° C. and still more preferably from 140 to 170° C.

The bottoms stream obtained from (K1) has a preferred methanol content of from 40 to 70 wt.-% and a preferred water content of from 30 to 60 wt.-%.

The top stream (M-di) obtained from column (K2) comprises at least 85 wt.-% of methanol and up to 10 wt.-% of water, more preferably at least 90 wt.-% of methanol and up to 10 wt.-% of water, more preferably at least 95 wt.-% of methanol and up to 5 wt.-% of water, more preferably at least 96 wt.-% of methanol and up to 4 wt.-% of water and especially preferably at least 97 wt.-% of methanol and up to 3 wt.-% of water. According to particularly preferred embodiment, the top stream obtained from column (K2) comprises less than 3 wt.-% of water such as, for example, from 1 to 2 wt.-% of water.

The mixture (M-dii) obtained from the bottom of column (K2) comprises at least 90 wt.-% of water, more preferably at least 95 wt.-% of water and especially preferably at least 97 wt.-% of water. Preferably (M-dii) is essentially free of methanol, i.e. it has a methanol content of less than 5 ppm, more preferably of less than 1 ppm. In addition to water, (M-dii) can comprise certain by-products resulting from one or more stages of the overall epoxidation process. Examples for such by-products are glycol compounds such as propylene glycols. These by-products can be contained in (M-dii) in an amount of up to 4 wt.-%, preferably up to 3 wt.-%.

According to the process of the present invention, it is possible that the mixture (M-cii) introduced into stage (d) comprises by-produces produced in at least one stage of the overall epoxidation process such as glycol ethers like methoxypropanols. As to these mixtures, it was surprisingly found that above-described two-pressure distillation, additionally comprising a dividing-wall column, allows, on the one hand, for producing (Td) used as main source of heat integration of the overall process, and simultaneously, on the other hand, for simultaneously separating these by-products from the methanol stream (Td) which is fed back as solvent into stage (a) and obtaining a mixture (M-dii) as described above having a very low content regarding these by-products of not more than 4 wt.-%, preferably not more than 3 wt.-%.

A mixture (M-diii) taken from the side-offtake of the dividing-wall column (K2) comprises at least 10 wt.-% of glycol ethers, more preferably at least 15 wt.-% of glycol ethers and especially preferably at least 20 wt.-% of glycol ethers. Still more preferably, (M-diii) has a methanol content of not more than 5 wt.-%, more preferably less than 2 wt.-%, more preferably not more than 2 wt.-% and especially preferably less than 2 wt.-%.

If the separation process according of stage (d) is performed using a two-pressure distillation using a conventional distillation column (K1) together with a dividing wall column (K2), wherein the bottoms stream obtained from (K1) is heated with the bottoms stream obtained from (K2), and wherein the condenser used to condense the top stream obtained from (K2) is simultaneously used as vaporizer of (K1), the energy balance of stage (d) can be significantly improved. Based on a one-pressure distillation using at least one conventional distillation column as standard of comparison, an energy saving of from 40 to 70%, preferably from 50 to 60% is possible, provided that mixtures (M-di) and (M-dii) having essentially the same composition are obtained in the one-pressure or the two-pressure processes. Thus, the two-pressure distillation process further improves heat integration of the overall epoxidation process.

According to a preferred embodiment of the present invention, heat integration of the process is still further improved by heating the feed stream fed into at least one distillation column of stage (d) with the bottoms stream of this column. More preferably, the feed stream fed into the second column, preferably the dividing wall column, is heated with bottoms stream obtained from this column. Still more preferably, the temperature of the feed stream fed into the dividing wall column is heated from a temperature of from 100 to 140° C., more preferably from 110 to 130° C. to a temperature of from 140 to 180° C., more preferably from 150 to 170° C.

Stage (x)

According to a preferred embodiment wherein
(a) propene is reacted with hydrogen peroxide in the presence of methanol as solvent in at least two reaction stages to obtain a mixture (M-a) comprising propylene oxide, unreacted propene, propane, methanol and water, wherein between at least two reaction stages, propylene oxide is separated by distillation;
(b) unreacted propene is separated from the mixture (M-a) by distillation to obtain a mixture (M-bi) comprising propane and at least 80 wt.-% of propene, and a mixture (M-bii) comprising methanol, water and at least 7 wt.-% of propylene oxide the process of the present invention additionally comprises a further stage (x) of separating propene from mixture (M-bi).

Optionally, prior to separation of propene from (M-bi), (M-bi) can be subjected to at least one further separation process where by-products resulting from the epoxidation reaction can be removed from the mixture, and/or be subjected to at least one cooling stage.

The mixture (M-bi) fed to the distillation process of stage (x) has a propene content of at least 85 wt.-%, still more preferably of from 85 to 90.

Separation according to stage (x) is preferably carried out in at least one distillation column, more preferably in one distillation column. Preferably, this column has of from 80 to 160, more preferably of from 90 to 140 and especially preferably of from 100 to 140 theoretical stages.

The distillation column is preferably operated at a top pressure of from 1 to 50 bar, more preferably of from 10 to 40 bar, more preferably of from 20 to 30 bar.

According to a still further preferred embodiment, a mixture (M-x) is obtained comprising at least 85 wt-% of olefin, still more preferably of from 85 to 90 wt.-% of olefin, preferably of propene.

More preferably, the mixture (M-x) comprises from 92 to 99 wt.-%, more preferably from 94 to 99 wt.-%, and especially preferably from 96 to 99 wt.-% of propene. Depending on the exact distillation conditions, (M-x) can be obtained at the top of the column or as a side stream of the distillation column. The propane content of (M-x) is preferably less than 5 wt.-%, more preferably less than 4 wt.-% and especially less than 3 wt.-%, based on the total weight of mixture (M-x).

Therefore, the present invention also relates to a process as described above, wherein in (a), the mixture (M-a) additionally comprises propane, wherein in (b), unreacted propene is separated from the mixture (M-a) by distillation to obtain the mixture (M-bi) comprising the unreacted propene and propane, said process additionally comprising
(x) separating the propene from the mixture (M-bi) by distillation to obtain a mixture (M-x) comprising at least 90 wt.-% of propene,
and wherein the vapor top stream (Td) is used to operate at least partially at least one vaporizer used in at least one distillation column used in at least one of stages (a), (b), (c) and (x).

Preferably, from 1 to 20 wt.-%, more preferably from 2 to 15 wt.-% and especially preferably from 3 to 10 wt.-% of (Td) are used to operate the vaporizer of the distillation column used in stage (x).

Therefore, the present invention also relates to a process as described above wherein from 5 to 60 wt.-% of (Td) are used to operate at least partially a vaporizer used in (a), from 1 to 20 wt.-% of (Td) are used to operate at least partially a vaporizer used in (b), from 1 to 50 wt.-% of (Td) are used to operate at least partially a vaporizer used in (c), and from 1 to 20 wt.-% of (Td) are used to operate at least partially a vaporizer used in (x).

Optionally, it is possible that the vaporizer of the distillation column of stage (x) is additionally operated by low pressure steam having, for example, a pressure of about 1.5 bar, or hot water.

According to a further preferred embodiment, mixture (M-x) is recycled and fed back as starting material stream into stage (a), either into at least one of the reactors used in stage (i) of stage (a) or into at least one of the reactors used in stage (iii) of stage (a) or into at least one of the reactors used in stage (i) and at least one of the reactors used in stage (iii) of stage (a).

Thus, stage (x) of the present invention not only provides an improvement regarding heat integration of the overall process but also an ideal possibility of recovering propene in a degree of purity so as to recycle propene as starting material for the epoxidation reaction. Hence, stage (x) provides an improvement of energy balance and simultaneously of material balance of the overall process.

If necessary, at least one feed stream fed into at least one distillation column used in stage (x) can be heated with the bottoms stream obtained from this column.

Stage (y)

According to the present invention, a mixture (M-cii) is obtained from stage (c) comprising of from 55 to 85 wt.-%, more preferably from 65 to 80 wt.-% and especially preferably from 75 to 80 wt.-% of methanol, and of from 15 to 45 wt.-%, more preferably from 20 to 35 wt.-% and especially preferably of from 20 to 25 wt.-% of water.

Mixture (M-cii) can further contain certain by-products resulting from one or more stages of the overall epoxidation process, having boiling points lower than water and lower than methanol. Examples for such by-products are aldehydes such as, for example, acetaldehyde and/or propionaldehyde, or other compounds such as dioxolanes. These by-products can be contained in (M-cii) in an amount of up to 0.3 wt.-%, preferably up to 0.15 wt.-% and especially preferably up to 0.12 wt.-%, based on the total weight of (M-cii) and referring to the sum of the respective weights of these low-boiling compounds.

Therefore, the present invention also relates to a process wherein prior to stage (d), at least one of these low boiling compounds is separated from mixture (M-cii) to give a mixture (M-y) which is then fed to stage (d).

In stage (y), at least one, preferably one distillation column is used. Preferably, this column has of from 2 to 40, more preferably of from 5 to 30 and especially preferably of from 10 to 25 theoretical stages.

The distillation column is preferably operated at a top pressure of from 1 to 2 bar, more preferably of from 1 to 1.5 bar, more preferably of from 1 to 1.2 bar. It was surprisingly found that choosing a distillation top pressure of this range allows for obtaining a high degree of purity of the bottoms stream with regard to the low boiling compounds, and simultaneously using at least partially (Td) to operate the vaporizer of the distillation column of stage (y).

Therefore, the present invention also relates to a process as described above, wherein in (c), the mixture (M-cii) additionally comprises at least one compound having a boiling temperature lower than methanol and lower than water at a given pressure, said process comprising
(y) separating the at least one compound having a boiling point lower than methanol and lower than water from the mixture (M-cii) by distillation to obtain a mixture (M-y) comprising from 40 to 80 wt.-% of methanol and from 10 to 55 wt.-% of water;

(d) separating methanol from the mixture (M-y) in at least one distillation stage to obtain a mixture (M-di) comprising at least 85 wt.-% of methanol and up to 10 wt.-% of water, and a mixture (M-dii) comprising at least 90 wt.-% of water, and wherein the vapor top stream (Td) is used to operate at least partially at least one vaporizer used in at least one distillation column used in at least one of stages (a), (b), (c) and (y).

Accordingly, the present invention also provides a process as described above, wherein from 5 to 60 wt.-% of (Td) are used to operate at least partially a vaporizer used in (a), from 1 to 20 wt.-% of (Td) are used to operate at least partially a vaporizer used in (b), from 1 to 50 wt.-% of (Td) are used to operate at least partially a vaporizer used in (c), and from 5 to 60 wt.-% of (Td) are used to operate at least partially a vaporizer used in (y).

More preferably, from 15 to 50 wt.-%, still more preferably from 20 to 40 wt.-% of (Td) are used to operate at least partially a vaporizer used in (y). Especially preferably, only (Td) is used to operate the vaporizer used in (y).

According to a still further preferred embodiment, a mixture (M-y) is obtained as bottoms stream comprising less than 0.06 wt.-%, more preferably less than 0.05 wt.-% and especially preferably less than 0.04 wt.-% of the low-boiling compounds, based on the total weight of (M-cii) and referring to the sum of the respective weights of these low-boiling compounds.

Thus, using only (Td) to operate the distillation column, it is possible to decrease the amount of low-boiling compounds for at least 50%, preferably more than 50%. Using no additional external energy source, the inventive process therefore allows for preventing these low-boiling compounds from exceeding undesirable concentrations in the methanol loop.

If necessary, at least one feed stream fed into at least one distillation column used in stage (y) can be heated with the bottoms stream obtained from this column.

In the context of the present invention, it was additionally found that the top stream obtained from the distillation column of stage (y) can be advantageously employed for operating at least one of the distillation columns in the overall epoxidation process. Most preferably, the top stream obtained from the distillation column of stage (y) is employed for operating at least one distillation column used in stage (c).

Therefore, the present invention also relates to a process according to the invention, wherein preferably from 1 to 80 wt.-%, more preferably from 10 to 60 wt.-% and still more preferably from 15 to 40 wt.-% of the top stream obtained from the distillation column of stage (y) are used to operate the vaporizer of the at least one distillation column of stage (c).

Stage (z)

According to another embodiment of the present invention, the by-products mentioned above which result from one or more stages of the overall epoxidation process and which have boiling points lower than water and lower than methanol, for example aldehydes such as, for example, acetaldehyde and/or propionaldehyde, or other compounds such as dioxolanes, which by-products can be contained in (M-cii) in an amount of up to 0.3 wt.-%, preferably up to 0.15 wt.-% and especially preferably up to 0.12 wt.-%, based on the total weight of (M-cii) and referring to the sum of the respective weights of these low-boiling compounds, can be separated in a stage (z) which is performed after stage (d).

Therefore, the present invention also relates to a process according to one of above-mentioned embodiments, wherein in (c), the mixture (M-cii) additionally comprises at least one compound having a boiling temperature lower than methanol and lower than water at a given pressure, said process comprising (d) separating methanol from the mixture (M-cii) in at least one distillation stage to obtain a mixture (M-di) comprising at least 85 wt.-% of methanol, up to 10 wt.-% of water and the at least one compound having a boiling temperature lower than methanol and lower than water, and a mixture (M-dii) comprising at least 90 wt.-% of water, (z) separating the compound having a boiling point lower than methanol and lower than water from the mixture (M-di) by distillation to obtain a mixture (M-z) comprising from 85 to 99.5 wt.-% of methanol and from 0.5 to 10 wt.-% of water;

and wherein the vapor top stream (Td) is used to operate at least partially at least one vaporizer used in at least one distillation column used in at least one of stages (a), (b), (c) and (z).

As to stage (d), reference is made to the paragraph above describing stage (d) and its preferred embodiments. Hence, stage (d) is preferably carried out using two, three or more columns, more preferably tow columns, still more preferably one conventional column (K1) and one dividing-wall column (K2), and especially preferably as two-pressure distillation using one conventional column (K1) and one dividing-wall column (K2), as described hereinabove.

Thus, especially if stage (d) is performed as two-pressure distillation using a conventional distillation column (K1) and a dividing wall column (K2), and wherein methanol is separated from the mixture (M-cii) to obtain a mixture (M-di) comprising at least 85 wt.-% methanol, up to 10 wt.-% of water and the at least one compound having a boiling temperature lower than methanol and lower than water, and a mixture (M-dii) comprising at least 90 wt-% of water, the top stream (Td) is obtained from (K1), and the mixture (M-di) is obtained as top stream from (K2), the mixture (M-dii) is obtained as bottoms stream from (K2) and the mixture (M-diii) is obtained from the side-offtake from (K2). The top stream (Td) is used as described above, and the condensate of (Td) resulting, for example, from at least one of the vaporizers as described hereinabove and hereinunder, said condensate containing the at least one compound having a boiling temperature lower than methanol and lower than water, is fed into stage (z) to obtain a mixture (M-z) as bottoms stream comprising from 85 to 99.5 wt.-% of methanol and from 0.5 to 10 wt.-% of water.

The mixture (M-dii) obtained from the bottom of column (K2) comprises at least 90 wt.-% of water, more preferably at least 95 wt.-% of water and especially preferably at least 97 wt.-% of water. Preferably (M-dii) is essentially free of methanol, i.e. it has a methanol content of less than 5 ppm, more preferably of less than 1 ppm. Additionally to water, (M-dii) can comprise certain by-products resulting from one or more stages of the overall epoxidation process. Examples for such by-products are glycol compounds such as propylene glycols. These by-products can be contained in (M-dii) in an amount of up to 4 wt.-%, preferably up to 3 wt.-%.

A mixture (M-diii) taken from the side-offtake of the dividing-wall column (K2) comprises at least 10 wt.-% of glycol ethers, more preferably at least 15 wt.-% of glycol ethers and especially preferably at least 20 wt.-% of glycol ethers. Still more preferably, (M-diii) has a methanol content of not more than 5 wt.-%, more preferably less than 2 wt.-%, more preferably not more than 2 wt.-% and especially preferably less than 2 wt.-%.

According to a still further preferred embodiment, mixture (M-di) obtained as top stream from (K2) is additionally fed into stage (z).

According to a further embodiment, a part of mixture (M-di) obtained as top stream from (K2) is fed as reflux to the top of column (K1).

According to a further embodiment, a part of the condensate of (Td) is fed as reflux to the top of column (K1).

According to a further embodiment, a part of mixture (M-di) obtained as top stream from (K2) and a part of the condensate of (Td) are fed as reflux to the top of column (K1).

Stage (z) is preferably carried out using one distillation column having, for example, from 2 to 40, preferably from 5 to 30 and especially preferably from 10 to 25 theoretical stages. Distillation is carried out at a preferred pressure of from 1 to 2 bar, more preferably from 1 to 1.5 bar and especially from 1 to 1.2 bar. It was surprisingly found that choosing a distillation top pressure of this range allows for obtaining a high degree of purity of the bottoms stream with regard to the low boiling compounds, and simultaneously using at least partially (Td) to operate the vaporizer of the distillation column of stage (z).

Accordingly, the present invention also provides a process as described above, wherein from 5 to 60 wt.-% of (Td) are used to operate at least partially a vaporizer used in (a), from 1 to 20 wt.-% of (Td) are used to operate at least partially a vaporizer used in (b), from 1 to 50 wt.-% of (Td) are used to operate at least partially a vaporizer used in (c), and from 5 to 60 wt.-% of (Td) are used to operate at least partially a vaporizer used in (z).

More preferably, from 15 to 50 wt.-%, still more preferably from 20 to 40 wt.-% of (Td) are used to operate at least partially a vaporizer used in (z). Especially preferably, only (Td) is used to operate the vaporizer used in (z).

According to a still further preferred embodiment, a mixture (M-z) is obtained as bottoms stream comprising less than 0.06 wt.-%, more preferably less than 0.05 wt.-% and especially preferably less than 0.04 wt.-% of the low-boiling compounds, based on the total weight of (M-cii) and referring to the sum of the respective weights of these low-boiling compounds. Further, (M-z) comprises at least 85 wt.-% of methanol and up to 10 wt.-% of water, more preferably at least 90 wt.-% of methanol and up to 10 wt.-% of water, more preferably at least 95 wt.-% of methanol and up to 5 wt.-% of water, more preferably at least 96 wt.-% of methanol and up to 4 wt.-% of water and especially preferably at least 97 wt.-% of methanol and up to 3 wt.-% of water. According to particularly preferred embodiment, (M-z) comprises less than 3 wt.-% of water such as, for example, from 1 to 2 wt.-% of water.

Mixture (M-z) is most preferably fed back as solvent into stage (a).

Thus, by using only (Td) to operate the distillation column of stage (z), it is possible to decrease the amount of low-boiling compounds for at least 50%, preferably more than 50%. Using no additional external energy source, the inventive process therefore allows for preventing these low-boiling compounds from exceeding undesirable concentrations in the methanol loop.

If necessary, at least one feed stream fed into at least one distillation column used in stage (z) can be heated with the bottoms stream obtained from this column.

The present invention also comprises an embodiment according to which a stage (y) is performed prior to stage (d) and simultaneously a stage (z) is performed after stage (d).

Stage (e)

According to stage (d), a mixture (M-dii) is obtained preferably comprising at least 90 wt.-% of water, more preferably at least 95 wt.-% of water and especially preferably at least 97 wt.-% of water. Preferably (M-dii) is essentially free of methanol, i.e. it has methanol content of less than 5 ppm, more preferably of less than 1 ppm. Additionally to water, (M-dii) can comprise certain by-products resulting from one or more stages of the overall epoxidation process. Examples for such by-products are glycol compounds such as propylene glycols. These by-products can be contained in (M-dii) in an amount of up to 4 wt.-%, preferably up to 3 wt.-%.

In order to separate at least one of these glycols from mixture (M-dii), it was surprisingly found that a vaporization process is suitable for this purpose, most preferably as part of a distillation process. In this context, it was found that vaporization can be performed using at least partially the methanol steam, i.e. top the stream (Td).

Therefore, the present invention also relates to a process as described above, additionally comprising (e) evaporating the mixture (M-dii).

Therefore, the present invention also relates to a process additionally comprising a stage (e), wherein from 5 to 60 wt.-% of (Td) are used to operate at least partially a vaporizer used in (a), from 1 to 20 wt.-% of (Td) are used to operate at least partially a vaporizer used in (b), from 1 to 50 wt.-% of (Td) are used to operate at least partially a vaporizer used in (c), and from 1 to 50 wt.-% of (Td) are used to operate at least partially a vaporizer used in (e).

Still more preferably, 10 to 40 wt.-%, especially preferably from 15 to 35 wt.-% of (Td) are used to operate at least one vaporizer used in stage (e).

Thus, yet another instrument is provided to still further improve the energy balance of the overall epoxidation process and simultaneously to recover a product of value, i.e. propylene glycol which can be separated having a degree of purity of preferably at least 80 wt.-% and a water content of preferably not more than 5 wt.-%, more preferably not more than 4 wt.-% and still more preferably not more than 3 wt.-%.

If necessary, a feed stream fed into a distillation column used in stage (e) can be heated with the bottoms stream obtained from this column.

According to a still further preferred embodiment of the present invention, the overall epoxidation process also encompasses, in addition to the heat exchangers used to at least partially transfer the heat contained in (Td) to the evaporators used in the distillation columns described above, at least one additional heat exchanger which serves as a control heat exchanger for the overall process.

Due to the number and various possibilities of improving the energy balance of the overall epoxidation process by using the methanol vapor (Td) as heat source for operating respective vaporizers in distillation columns, it was found that this at least one additional heat exchanger serves as an ideal instrument to remove part of (Td) if, at a given point in time, more (Td) is produced in stage (d) than the needs of the overall process requires. In this case, surplus (Td) is fed into the at least one control heat exchanger from which a methanol stream can be obtained which is recycled into stage (a) as solvent.

Therefore, the present invention also provides a process as described above, additionally comprising at least one control heat exchanger.

According to a preferred embodiment, from 1 to 50 wt.-% of (Td), more preferably from 2 to 40 wt.-% of (Td) and especially preferably from 3 to 30 wt.-% of (Td) are used at least partially as feed stream of at least one control heat exchanger and therefore to operate said at least one control heat exchanger used in the process.

According to a preferred embodiment of the present invention, the methanol vapor (Td) used to operate the vaporizers of the distillation columns, as described above, is subsequently re-used, optionally after collecting and/or storing, as solvent in stage (a) of the process. Alternatively or additionally, it can be used in at least one further process. Most preferably, it is recycled into the inventive epoxidation process thus improving the energy balance of the overall process and simultaneously the material balance of the overall balance.

According to yet another embodiment of the present invention, the inventive process comprises still another control heat exchanger which can act as counterpart of above-described control heat exchanger (fly wheel exchanger). This additional heat exchanger can serve as a source of methanol steam in case at a given point in time, there is not enough (Td) produced in stage (d) to meet the needs of the overall process. In this case, fresh methanol and/or methanol condensate obtained from (Td) after having served as heat source in the process, optionally collected and stored, can be fed to this additional control heat exchanger where methanol steam is produced. As heat source of this additional control heat exchanger, each suitable stream can be used. Most preferred is water steam.

Therefore, the present invention also relates to an epoxidation process comprising two heat exchangers acting as counterparts for meeting the needs of the epoxidation process regarding methanol steam as heat source for operating the distillation columns as described above.

Thus, by providing two counterpart control heat exchangers, the present invention provides a flexible instrument to meet, at any given point in time, the actual needs of the process regarding methanol steam as heat source.

As already described above, the present invention also provides a process wherein the feed of at least one distillation column used in stages (a), (b), (c), and (d), optionally also at least one of stages (x), (y) and (e), is heated with the bottom stream of this distillation column. Most preferably, at least one distillation column used in stages (a) and (d) is heated with the bottom stream of this distillation column.

In addition to the heat integration improvements described above, i.e. the inventive process encompassing an effective use of the methanol steam (Td), optionally together with an effective use of certain bottoms streams for heating feed streams, it was found that the overall process can be further improved by specific condensation stages wherein top streams obtained from specific columns are condensed in more than one stages, most preferably in two stages.

Therefore, the present invention also provides a process according to any one of above-mentioned embodiments, wherein the top stream obtained from at least one distillation column used in stages (a), (b), and (c), optionally additionally in at least one of stages (x), (y) and (e), is condensed in two stages, wherein in the first stage, the condenser is cooled with water having an inlet temperature of from 15 to 40° C. and in the second stage, the condenser is cooled with water having an inlet temperature of from 5 to 20° C., wherein the inlet temperature of the water used in the second stage is lower than the inlet temperature of the water used in the first stage.

Most preferably, this two-stage condensation is applied to the top streams obtained from the columns used in stages (b) and (c).

Therefore, the present invention also provides a process according to any one of above-mentioned embodiments, wherein in (c), the olefin oxide is separated in two distillation columns, and wherein from 0 to 20 wt.-% of (Td) is used to at least partially operate a vaporizer of the first distillation column from which a mixture comprising at least 98 wt.-% of olefin oxide is obtained, said mixture being introduced into the second distillation column, and from 1 to 30 wt.-% of (Td) are used to at least partially operate a vaporizer of the second distillation column from which an olefin oxide stream comprising at least 99.8 wt.-% olefin oxide is obtained, said olefin oxide stream comprising at least 99.8 wt.-% olefin oxide being condensed in two stages, wherein in the first stage, the condenser is cooled with water having an inlet temperature of from 15 to 40° C. and in the second stage, the condenser is cooled with water having an inlet temperature of from 5 to 20° C., wherein the inlet temperature of the water used in the second stage is lower than the inlet temperature of the water used in the first stage.

In the following, preferred processes of the present invention are listed resulting from the following embodiments 1 to 22 including the combinations of these embodiments as explicitly given:

1. A process for the epoxidation of an olefin comprising
   (a) reacting the olefin with hydrogen peroxide in the presence of methanol as solvent in at least two reaction stages to obtain a mixture (M-a) comprising olefin oxide, unreacted olefin, methanol and water, wherein between at least two reaction stages, olefin oxide is separated by distillation;
   (b) separating unreacted olefin from the mixture (M-a) by distillation to obtain a mixture (M-bi) comprising at least 80 wt.-% of olefin and a mixture (M-bii) comprising methanol, water and at least 7 wt.-% of olefin oxide;
   (c) separating olefin oxide from the mixture (M-bii) in at least one distillation stage to obtain a mixture (M-ci) comprising at least 99 wt.-% of olefin oxide and a mixture (M-cii) comprising water and at least 55 wt.-% of methanol;
   (d) separating methanol from the mixture (M-cii) in at least one distillation stage to obtain a mixture (M-di) comprising at least 85 wt.-% of methanol and up to 10 wt.-% of water, and a mixture (M-dii) comprising at least 90 wt.-% of water;
   wherein a vapor top stream (Td) obtained from at least one distillation column used in (d), said vapor top stream (Td) comprising at least 85 wt.-% methanol, is used to operate at least partially at least one vaporizer used in at least one distillation column used in at least one of stages (a), (b) and (c).

2. The process according to embodiment 1, wherein from 5 to 60 wt.-% of (Td) are used to operate at least partially a vaporizer used in (a), from 1 to 20 wt.-% of (Td) are used to operate at least partially a vaporizer used in (b), and from 1 to 50 wt.-% of (Td) are used to operate at least partially a vaporizer used in (c).

3. The process according to embodiment 1, wherein the olefin is propene and the olefin oxide is propylene oxide.

4. The process according to embodiment 3, wherein in (a), the mixture (M-a) additionally comprises propane, wherein in (b), unreacted propene is separated from the mixture (M-a) by distillation to obtain the mixture (M-bi) comprising the unreacted propene and propane, said process additionally comprising (x) separating the propene from the mixture (M-bi) by distillation to obtain a mixture (M-x) comprising at least 90 wt.-% of propene, and wherein the vapor top stream (Td) is used to operate at least partially at least one vaporizer used in at least one distillation column used in at least one of stages (a), (b), (c) and (x).

5. The process according to embodiment 4, wherein from 5 to 60 wt.-% of (Td) are used to operate at least partially a vaporizer used in (a), from 1 to 20 wt.-% of (Td) are used to operate at least partially a vaporizer used in (b), from 1 to 50 wt.-% of (Td) are used to operate at least partially a vaporizer used in (c), and from 1 to 20 wt.-% of (Td) are used to operate at least partially a vaporizer used in (x).

6. The process according to embodiment 3, wherein in (c), the mixture (M-cii) additionally comprises at least one compound having a boiling temperature lower than methanol and lower than water at a given pressure, said process comprising (y) separating the at least one compound having a boiling point lower than methanol and lower than water from the mixture (M-cii) by distillation to obtain a mixture (M-y) comprising from 40 to 80 wt.-% of methanol and from 10 to 55 wt.-% of water;

(d) separating methanol from the mixture (M-y) in at least one distillation stage to obtain a mixture (M-di) comprising at least 85 wt.-% of methanol and up to 10 wt.-% of water, and a mixture (M-dii) comprising at least 90 wt.-% of water, and wherein the vapor top stream (Td) is used to operate at least partially at least one vaporizer used in at least one distillation column used in at least one of stages (a), (b), (c) and (y).

7. The process according to embodiment 6, wherein from 5 to 60 wt.-% of (Td) are used to operate at least partially a vaporizer used in (a), from 1 to 20 wt.-% of (Td) are used to operate at least partially a vaporizer used in (b), from 1 to 50 wt.-% of (Td) are used to operate at least partially a vaporizer used in (c), and from 5 to 60 wt.-% of (Td) are used to operate at least partially a vaporizer used in (y).

8. The process according to embodiment 3, wherein in (c), the mixture (M-cii) additionally comprises at least one compound having a boiling temperature lower than methanol and lower than water at a given pressure, said process comprising (d) separating methanol from the mixture (M-cii) in at least one distillation stage to obtain a mixture (M-di) comprising at least 85 wt.-% of methanol, up to 10 wt.-% of water and the at least one compound having a boiling temperature lower than methanol and lower than water, and a mixture (M-dii) comprising at least 90 wt.-% of water, (z) separating the compound having a boiling point lower than methanol and lower than water from the mixture (M-di) by distillation to obtain a mixture (M-z) comprising from 85 to 99.5 wt.-% of methanol and from 0.5 to 10 wt.-% of water;

and wherein the vapor top stream (Td) is used to operate at least partially at least one vaporizer used in at least one distillation column used in at least one of stages (a), (b), (c) and (z).

9. The process according to embodiment 8 wherein from 5 to 60 wt.-% of (Td) are used to operate at least partially a vaporizer used in (a), from 1 to 20 wt.-% of (Td) are used to operate at least partially a vaporizer used in (b), from 1 to 50 wt.-% of (Td) are used to operate at least partially a vaporizer used in (c), and from 5 to 60 wt.-% of (Td) are used to operate at least partially a vaporizer used in (z).

10. The process according to embodiment 1, wherein in (c), the olefin oxide is separated in two distillation columns, and wherein from 0 to 20 wt.-% of (Td) is used to at least partially operate a vaporizer of the first distillation column from which a mixture comprising at least 98 wt.-% of olefin oxide is obtained, said mixture being introduced into the second distillation column, and from 1 to 30 wt.-% of (Td) are used to at least partially operate a vaporizer of the second distillation column from which an olefin oxide stream comprising at least 99.8 wt.-% olefin oxide is obtained.

11. The process according to embodiment 1, additionally comprising (e) evaporating the mixture (M-dii).

12. The process according to embodiment 11, wherein from 5 to 60 wt.-% of (Td) are used to operate at least partially a vaporizer used in (a), from 1 to 20 wt.-% of (Td) are used to operate at least partially a vaporizer used in (b), from 1 to 50 wt.-% of (Td) are used to operate at least partially a vaporizer used in (c), and from 1 to 50 wt.-% of (Td) are used to operate at least partially a vaporizer used in (e).

13. The process according to embodiment 1, wherein from 1 to 50 wt.-% of (Td) are used to at least partially operate at least one control heat exchanger used in the process.

14. The process according to embodiment 1, wherein the feed of at least one distillation column used in stages (a), (b), (c), and (d) is heated with the bottom stream of this distillation column.

15. The process according to embodiment 1, wherein the top stream obtained from at least one distillation column used in stages (a), (b), and (c) is condensed in two stages, wherein in the first stage, the condenser is cooled with water having an inlet temperature of from 15 to 40° C. and in the second stage, the condenser is cooled with water having an inlet temperature of from 5 to 20° C., wherein the inlet temperature of the water used in the second stage is lower than the inlet temperature of the water used in the first stage.

16. The process according to embodiment 15, wherein in (c), the olefin oxide is separated in two distillation columns, and wherein from 0 to 20 wt.-% of (Td) are used to at least partially operate a vaporizer of the first distillation column from which a mixture comprising at least 98 wt.-% of olefin oxide is obtained, said mixture being introduced into the second distillation column, and from 1 to 30 wt.-% of (Td) are used to at least partially operate a vaporizer of the second distillation column from which an olefin oxide stream comprising at least 99.8 wt.-% olefin oxide is obtained, said olefin oxide stream comprising at least 99.8 wt.-% olefin oxide being condensed in two stages, wherein in the first stage, the condenser is cooled with water having an inlet temperature of from 15 to 40° C. and in the second stage, the condenser is cooled with water having an inlet temperature of from 5 to 20° C., wherein the inlet temperature of the water used in the second stage is lower than the inlet temperature of the water used in the first stage.

17. The process according to embodiment 1, wherein in (d), methanol is separated from the mixture (M-cii) in a two pressure distillation process, where in a first distillation column, distillation is carried out at a top pressure which is different from the top pressure of a second distillation column and wherein the condenser used to condense the top stream of the first or second distillation column is used simultaneously as the vaporizer of the second or first distillation column.

18. The process according to embodiment 17, wherein the top pressure of the first distillation column is from 2 to 8 bar and the top pressure of the second distillation column is from 8 to 15 bar.
19. The process according to embodiment 1, wherein in (d),
   (i) the mixture (M-cii) is introduced into a first distillation column (K1) from which the vapor top stream (Td) is obtained, the distillation in (K1) being carried out at a top pressure of from 2.5 to 6 bar; and
   (ii) the bottoms stream obtained from (K1) is introduced into a second distillation column (K2), the distillation in (K2) being carried out at a top pressure of from 9 to 13 bar,
   wherein prior to introducing into (K2), the bottoms stream obtained from (K1) is heated to a temperature from 110 to 180° C. with the bottoms stream obtained from (K2), and wherein the condenser used to condense the top stream obtained from (K2) is simultaneously used as vaporizer of (K1).
20. The process according to embodiment 19, wherein (K2) is a dividing wall column.
21. The process according to embodiment 1, wherein the olefin separated in (b) is re-introduced into (a).
22. The process according to embodiment 1, wherein the methanol separated in (d) is re-introduced into (a).

According to an especially preferred embodiment, the present invention provides a process for the epoxidation of propene, comprising
(a) reacting the propene with hydrogen peroxide in the presence of methanol as solvent in at least two reaction stages to obtain a mixture (M-a) comprising propylene oxide, unreacted propene, propane, methanol and water, wherein between at least two reaction stages, propylene oxide is separated by distillation;
(b) separating unreacted propene from the mixture (M-a) by distillation to obtain a mixture (M-bi) comprising propane and at least 80 wt.-% of propene, and a mixture (M-bii) comprising methanol, water and at least 7 wt.-% of propylene oxide;
(x) separating propene from the mixture (M-bi) by distillation to obtain a mixture (M-x) comprising at least 95 wt.-% of propene, and re-introducing (M-x) into (a);
(c) separating the propylene oxide from the mixture (M-bii) in at least one distillation stage to obtain a mixture (M-ci) comprising at least 99 wt.-% of propylene oxide and a mixture (M-cii) comprising water, at least one compound having a boiling temperature lower than methanol and lower than water at a given pressure, and at least 60 wt.-% of methanol;
(y) separating the at least one compound having a boiling point lower than methanol and lower than water from the mixture (M-cii) by distillation to obtain a mixture (M-y) comprising from 40 to 80 wt.-% of methanol and from 10 to 55 wt.-% of water;
(d) separating methanol from the mixture (M-y) in at least one distillation stage to obtain a mixture (M-di) comprising at least 85 wt.-% of methanol and up to 10 wt.-% of water, and a mixture (M-dii) comprising at least 90 wt.-% of water, and re-introducing (M-di) into (a);
(e) evaporating the mixture (M-dii),
wherein a vapor top stream (Td) is obtained from at least one distillation column used in (d), said vapor top stream (Td) comprising at least 85 wt.-% methanol, and wherein from 15 to 50 wt.-% of (Td) are used to operate at least partially a vaporizer used in (a), from 2 to 15 wt.-% of (Td) are used to operate at least partially a vaporizer used in (b), from 1 to 10 wt.-% of (Td) are used to operate at least partially a vaporizer used in (x), from 2 to 40 wt.-% of (Td) are used to operate at least partially a vaporizer used in (c), from 15 to 50 wt.-% of (Td) are used to operate at least partially a vaporizer used in (y), and from 10 to 40 wt.-% of (Td) are used to operate at least partially a vaporizer used in (e).

As to this embodiment, it is still further preferred that in (c), the propylene oxide is separated in two distillation columns, and wherein from 0 to 20 wt.-% of (Td) are used to at least partially operate a vaporizer of the first distillation column from which a mixture comprising at least 98 wt.-% of propylene oxide is obtained, said mixture being introduced into the second distillation column, and from 1 to 30 wt.-% of (Td) are used to at least partially operate a vaporizer of the second distillation column from which an propylene oxide stream comprising at least 99.8 wt.-% propylene oxide is obtained.

Additionally or alternatively to the separation in two distillation columns, this embodiment comprises at least one further integration method selected from the group consisting of
(I) using 1 to 40 wt.-% of (Td) to at least partially operate at least one control heat exchanger used in the process;
(II) heating the feed of at least one distillation column used in stages (a), (b), (x), (c), (y), (d) and (e) with the bottom stream of this distillation column; and
(III) condensing the top stream obtained from at least one distillation column used in stages (a), (b), (x), (c), (y), and (e) in two stages, wherein in the first stage, the condenser is cooled with water having an inlet temperature of from 15 to 40° C. and in the second stage, the condenser is cooled with water having an inlet temperature of from 5 to 20° C., wherein the inlet temperature of the water used in the second stage is lower than the inlet temperature of the water used in the first stage.

Additionally or alternatively to the separation in two distillation columns and at least one of the methods (I) to (III), this embodiment comprises a preferred embodiment of stage (d), according to which
(i) the mixture (M-y) is introduced into a first distillation column (K1) from which the vapor top stream (Td) is obtained, the distillation in (K1) being carried out at a top pressure of from 2.5 to 6 bar; and
(ii) the bottoms stream obtained from (K1) is introduced into a second distillation column (K2), most preferably a dividing wall column (K2), the distillation in (K2) being carried out at a top pressure of from 9 to 13 bar,
wherein prior to introducing into (K2), then bottoms stream obtained from (K1) is heated to a temperature from 120 to 180° C. with the bottoms stream obtained from (K2), and wherein the condenser used to condense the top stream obtained from (K2) is simultaneously used as vaporizer of (K1).

According to a still further preferred embodiment, the present invention provides a process for the epoxidation of propene, comprising
(a) reacting the propene with hydrogen peroxide in the presence of methanol as solvent in at least two reaction stages to obtain a mixture (M-a) comprising propylene oxide, unreacted propene, propane, methanol and water, wherein between at least two reaction stages, propylene oxide is separated by distillation in a divided wall column, wherein separated methanol is recycled into (a);
(b) separating unreacted propene from the mixture (M-a) by distillation to obtain a mixture (M-bi) comprising propane and at least 80 wt.-% of propene, and a mixture (M-bii) comprising methanol, water and at least 7 wt.-% of propylene oxide;

(x) separating propene from the mixture (M-bi) by distillation to obtain a mixture (M-x) comprising at least 95 wt.-% of propene, and re-introducing (M-x) into (a);
(c) separating the propylene oxide from the mixture (M-bii) in two distillation columns, wherein from the first distillation column, a first mixture comprising at least 99 wt.-% of propylene oxide and a mixture (M-cii) comprising water, at least one compound having a boiling temperature lower than methanol and lower than water at a given pressure, and at least 60 wt.-% of methanol, are obtained, said first mixture being introduced into the second distillation column from which a mixture (M-ci) comprising at least 99.8 wt.-% propylene oxide is obtained;
(y) separating the at least one compound having a boiling point lower than methanol and lower than water from the mixture (M-cii) by distillation to obtain a mixture (M-y) comprising from 40 to 80 wt.-% of methanol and from 10 to 55 wt.-% of water;
(d) separating methanol from the mixture (M-y) wherein
  (i) the mixture (M-y) is introduced into a first distillation column (K1) from which the vapor top stream (Td) is obtained, the distillation in (K1) being carried out at a top pressure of from 2.5 to 6 bar; and
  (ii) the bottoms stream obtained from (K1) is introduced into a second distillation column (K2), the distillation in (K2) being carried out at a top pressure of from 9 to 13 bar, (K2) being a dividing wall column,
  and wherein, prior to introducing into (K2), the bottoms stream obtained from (K1) is heated to a temperature from 130 to 175° C. with the bottoms stream obtained from (K2), and wherein the condenser used to condense the top stream obtained from (K2) is simultaneously used as vaporizer of (K1), and wherein (Td) and the top stream obtained from (K2) are re-introduced into (a);
(e) evaporating the mixture (M-dii),
wherein a vapor top stream (Td) obtained from at least one distillation column used in (d), said vapor top stream (Td) comprising at least 85 wt.-% methanol, is used to operate at least partially at least one vaporizer used in at least one distillation column used in at least one of stages (a), (b), (c), (e), (x) and (y).

As to this embodiment, it is still further preferred that from 15 to 50 wt.-% of (Td) are used to operate at least partially a vaporizer used in (a), from 2 to 15 wt.-% of (Td) are used to operate at least partially a vaporizer used in (b), from 2 to 15 wt.-% of (Td) are used to operate at least partially a vaporizer used in (x), from 0 to 15 wt.-% of (Td) are used to operate at least partially a vaporizer used in the first distillation column in (c), from 2 to 25 wt.-% of (Td) are used to operate at least partially a vaporizer used in the second distillation column in (c), from 15 to 50 wt.-% of (Td) are used to operate at least partially a vaporizer used in (y), and from 2 to 20 wt.-% of (Td) are used to operate at least partially a vaporizer used in (e).

Additionally or alternatively, this embodiment comprises at least one further integration method selected from the group consisting of
(I) using 1 to 50 wt.-% of (Td), more preferably 2 to 40 wt.-% of (Td) and still more preferably from 3 to 30 wt.-% of (Td) to at least partially operate at least one control heat exchanger used in the process;
(II) heating the feed of at least one distillation column used in stages (a), (b), (x), (c), (y), (d) and (e), preferably in stages (a) and/or (d), with the bottom stream of this distillation column; and
(III) condensing the top stream obtained from at least one distillation column used in stages (a), (b), (x), (c), (y), and (e), more preferably in stages (b) and/or (c), in two stages, wherein in the first stage, the condenser is cooled with water having an inlet temperature of from 15 to 40° C. and in the second stage, the condenser is cooled with water having an inlet temperature of from 5 to 20° C., wherein the inlet temperature of the water used in the second stage is lower than the inlet temperature of the water used in the first stage.

According to a still further preferred embodiment, the present invention provides a highly integrated process for the epoxidation of propene, comprising
(a) reacting the propene with hydrogen peroxide in the presence of methanol as solvent in at least two reaction stages to obtain a mixture (M-a) comprising propylene oxide, unreacted propene, propane, methanol and water, wherein between at least two reaction stages, propylene oxide is separated by distillation;
(b) separating unreacted propene from the mixture (M-a) by distillation to obtain a mixture (M-bi) comprising propane and at least 80 wt.-% of propene, and a mixture (M-bii) comprising methanol, water and at least 7 wt.-% of propylene oxide;
(x) separating propene from the mixture (M-bi) by distillation to obtain a mixture (M-x) comprising at least 95 wt.-% of propene, and re-introducing (M-x) into (a);
(c) separating the propylene oxide from the mixture (M-bii) in two distillation columns, wherein from the first distillation column, a first mixture comprising at least 99 wt.-% of propylene oxide and a mixture (M-cii) comprising water, at least one compound having a boiling temperature lower than methanol and lower than water at a given pressure and at least 60 wt.-% of methanol, are obtained, said first mixture being introduced into the second distillation column from which a mixture (M-ci) comprising at least 99.8 wt.-% propylene oxide is obtained;
(y) separating the at least one compound having a boiling point lower than methanol and lower than water from the mixture (M-cii) by distillation to obtain a mixture (M-y) comprising from 40 to 80 wt.-% of methanol and from 10 to 55 wt.-% of water;
(d) separating methanol from the mixture (M-y) wherein
  (i) the mixture (M-y) is introduced into a first distillation column (K1) from which the vapor top stream (Td) is obtained, the distillation in (K1) being carried out at a top pressure of from 2.5 to 6 bar; and
  (ii) the bottoms stream obtained from (K1) is introduced into a second distillation column (K2), the distillation in (K2) being carried out at a top pressure of from 9 to 13 bar, (K2) being a dividing wall column,
  and wherein, prior to introducing into (K2), the bottoms stream obtained from (K1) is heated to a temperature from 140 to 170° C. with the bottoms stream obtained from (K2), and wherein the condenser used to condense the top stream obtained from (K2) is simultaneously used as vaporizer of (K1), and wherein (Td) and the top stream obtained from (K2) are re-introduced into (a);
(e) evaporating the mixture (M-dii),
wherein a vapor top stream (Td) obtained from at least one distillation column used in (d), said vapor top stream (Td) comprising at least 85 wt.-% methanol, wherein from 20 to 40 wt-% of (Td) are used to operate at least partially a vaporizer used in (a), from 3 to 10 wt.-% of (Td) are used to operate at least partially a vaporizer used in (b), from 3 to 10 wt.-% of (Td) are used to operate at least partially a vaporizer used in (x), from 0 to 10 wt.-% of (Td) are used to operate at least partially a vaporizer used in the first distillation column in (c), from 2 to 20 wt.-% of (Td) are used to operate at least partially a vaporizer used in the second distillation column in (c), from 20 to 40 wt.-% of (Td) are used to operate at least partially a vaporizer used in (y), from 15 to 35 wt.-% of (Td) are used to operate at least partially a vaporizer used in (e), and from 3 to 30 wt.-% of (Td) are used to at least partially operate at least one control heat exchanger used in the process, said process further comprising at least one further integration method selected from the group consisting of (II) heating the feed of the distillation column used in stage (a) with the bottoms stream of this column and the feed of at least one distillation column used in stage (d) with the bottoms stream of this column;

(III) condensing the top stream obtained from at least one distillation column used in stages (a), (b), (x), (c), (y), and (e) in two stages, wherein in the first stage, the condenser is cooled with water having an inlet temperature of from 15 to 40° C. and in the second stage, the condenser is cooled with water having an inlet temperature of from 5 to 20° C., wherein the inlet temperature of the water used in the second stage is lower than the inlet temperature of the water used in the first stage.

EXAMPLES

Example 1

Heat-Integrated Process According to the Invention, Comprising Stages (a), (b), (c), and (d)

Propylene (chemical grade) is converted to propylene oxide with crude hydrogen peroxide having a concentration of 40 wt.-% in the presence of methanol as solvent and TS-1 catalyst in two reaction stages (i) and (iii), wherein between the two reaction stages, propylene oxide is separated in a stage (ii) by distillation.

Reaction in stage (i) is performed at 20 bar, in stage (iii) at 10 bar. $H_2O_2$ conversion in stage (i) is 91%. The distillation is running at a top pressure of 1.2 bar. From the divided wall column in stage (ii) (40 theoretical stages, dividing wall from stage 8 to 32), a stream containing surplus propylene and propylene oxide is separated by distillation over the top. The side stream with a concentration of 98 wt.-% methanol and 2 wt.-% $H_2O$ is directly recycled to reaction stage (i) in an amount of 13.5% of the MeOH solvent stream applied in the process. The bottom stream containing methanol, water, unreacted hydrogen peroxide and epoxidation byproducts, e.g. glycolethers, is sent together with fresh propylene to reaction stages (iii) to convert $H_2O_2$ to 99.9%. The stream (M-a) is a mixture of the distillation top stream and the outlet stream of stage (iii) and comprises olefin oxide, unreacted olefin, methanol and water. (M-a) is sent to stage (b).

The unreacted olefin from the mixture (M-a) is separated by distillation (b) in a distillation column with 14 theoretical stages at a pressure of 1.1 bar to obtain a mixture (M-bi) at the top of the column comprising 89 wt.-% olefin, 5.6 wt.-% of propane, 4 wt.-% methanol and 1.4 wt.-% oxygen and to obtain further a mixture (M-bii) comprising methanol, water and 11.1 wt.-% of olefin oxide.

Subsequently, the crude olefin oxide is separated from the mixture (M-bii) in a distillation stage (c) at 0.5 bar in a distillation tower having 80 theoretical stages to obtain a top mixture (M-ci) comprising 99.8 wt.-% of olefin oxide, 0.04 wt.-% of propylene, 0.04 wt.-% of acetaldehyde, 0.01 wt.-% of methanol, 0.01 wt.-% of methanol and a mixture (M-cii) comprising 76.2 wt.-% of methanol, 22.7 wt.-% water; the rest being heavy boiling byproducts of the epoxidation. The pure olefin oxide (>99.9 wt.-% propylene oxide) is separated from the mixture (M-ci) by distillation at a pressure of 4 bar in a distillation tower having 45 theoretical stages as a side stream product from theoretical stage 5.

The solvent methanol is separated from the mixture (M-cii) in two thermally coupled distillation columns in a stage (d). (M-cii) is introduced into a first distillation column (13 theoretical stages) from which the vapor top stream (Td) is obtained, the distillation being carried out at a top pressure of 3.9 bar. The bottoms stream obtained is introduced into a second distillation column, a divided wall column (40 theoretical stages, dividing wall from stage 6 to stage 30), the distillation being carried out at a top pressure of 10.8 bar. Two thermally coupled distillation towers are realized such that the condenser used to condense the top stream obtained of the second tower is simultaneously used as vaporizer for the first column. The mixture (M-di) (liquid top product of the second column) comprises 98 wt.-% of methanol and 2 wt.-% of water, the mixture (M-dii) (bottom product of the second column) comprises 97.5 wt.-% of water, 2 wt.-% propylene glycol, 0.05 wt.-% monoglycol ethers, 0.45 wt.-% higher glycol ethers, and the mixture (M-diii) (side stream product of the second column) comprises 22 wt.-% glycol ethers and 88 wt.-% water. The second methanol/water separation column is operated with 16 bar steam (water steam) from the grid.

The top vapor stream (Td), obtained from the first distillation column used in (d) having a pressure of 3.9 bar and a temperature of 104° C., and comprising 98 wt.-% of methanol and 2 wt.-% of water, is used to operate the vaporizers (reboilers) used in the distillation column used as mentioned in the separation stages (a), (b) and (c).

The following heat duties, calculated per metric ton/h recycled methanol as solvent, are needed to operate the above-described process:

A heat duty of 428 KW/($t_{MeOH}$/h) is necessary. Stage (ii) consumes 37% (a heat duty of 158 KW/($t_{MeOH}$/h)), stage (b) consumes 5% (a heat duty of 21 KW/($t_{MeOH}$/h)), stage (c) consumes 12% (a heat duty of 50 KW/($t_{MeOH}$/h)) of the MeOH-vapour top stream (Td), obtained from the first distillation column used in (d) having a pressure of 3.9 bar and a temperature of 104° C.

Example 2

Process According to the Prior Art, Comprising Stages (a), (b), (c), and (d) Without Heat Integration Comparative Example Propylene (chemical grade) is converted to propylene oxide with crude hydrogen peroxide having a concentration of 40 wt.-% in the presence of methanol as solvent and TS-1 catalyst in two reaction stages (i) and (iii), wherein between the two reaction stages propylene oxide is separated in a stage (ii) by distillation.

Reaction in stage (i) is performed at 20 bar, in stage (iii) at 10 bar. $H_2O_2$ conversion in stage (i) is 91%. The distillation is running at top pressure of 1.2 bar. From the divided wall column in stage (ii) (40 theoretical stages, dividing wall from stage 8 to 32), a stream containing surplus propylene and propylene oxide is separated by distillation over the top. The side stream with a concentration of 98 wt.-% methanol and 2 wt.-% $H_2O$ is directly recycled to reaction stage (i) in an amount of 13.5% of the MeOH solvent stream applied in the process. The bottom stream containing methanol, water, unreacted hydrogen peroxide and epoxidation byproducts, e.g. glycolethers, is sent together with fresh propylene to reaction stages (iii) to convert $H_2O_2$ to 99.9%. Stream (M-a)

is a mixture of the distillation top stream and the outlet stream of stage (iii) and comprises olefin oxide, unreacted olefin, methanol and water. (M-a) is sent to stage (b).

The unreacted olefin is separated from the mixture (M-a) by distillation (b) in a distillation column with 14 theoretical stages at a pressure of 1.1 bar to obtain a mixture (M-bi) at the top of the column comprising 89 wt.-% of olefin, 5.6 wt.-% of propane, 4 wt.-% methanol and 1.4 wt-% of oxygen, and a mixture (M-bii) comprising methanol, water and 11.1 wt.-% of olefin oxide.

Subsequently, the crude olefin oxide is separated from the mixture (M-bii) in a distillation stage (c) at 0.5 bar in a distillation tower having 80 theoretical stages to obtain a top mixture (M-ci) comprising 99.8 wt.-% of olefin oxide 0.04 wt.-% of propylene, 0.04 wt.-% of acetaldehyde, 0.01 wt.-% of methanol, 0.01 wt.-% of methanol and a mixture (M-cii) comprising 76.2 wt.-% of methanol, 22.7 wt.-% water; the rest being heavy boiling byproducts of the epoxidation. The pure olefin oxide (>99.9 wt.-% propylene oxide) is separated from the mixture (M-ci) by distillation at a pressure of 4 bar in a distillation tower having 45 theoretical stages as a side stream product from theoretical stage 5.

The solvent methanol is separated from the mixture (M-cii) in a stage (d) in two thermally coupled distillation columns. (M-cii) is introduced into a first distillation column (13 theoretical stages) from which the vapor top stream (Td) is obtained, the distillation being carried out at a top pressure of 3.9 bar. The bottoms stream obtained is introduced into a second distillation column, a divided wall column (40 theoretical stages, dividing wall from stage 6 to stage 30), the distillation being carried out at a top pressure of 10.8 bar. Two thermally coupled distillation towers as realized such that the condenser used to condense the top stream obtained of the second tower is simultaneously used as vaporizer for the first column. The mixture (M-di) (liquid top product of the second column) comprises 98 wt.-% of methanol and 2 wt.-% of water, the mixture (M-dii) (bottom product of the second column) comprises 97.5 wt.-% of water, 2 wt.-% propylene glycol, 0.05 wt.-% monoglycol ethers, 0.45 wt.-% higher glycol ethers, and the mixture (M-diii) (side stream product of the second column) comprises 22 wt.-% glycol ethers, and 88 wt.-% water. The second methanol/water separation column is operated with 16 bar steam (water steam) from the grid.

In contrast to example 1, water steam from grid is used to operate vaporizers (reboilers) used in distillation column as mentioned in the separation stages (a), (b) and (c).

The following heat duties, calculated per metric ton/h recycled methanol as solvent, are needed to operate the above-described process:

A heat duty of 676 KW/($t_{MeOH}$/h) is necessary. Stage (a) consumes additionally a heat duty of 158 KW/($t_{MeOH}$/h), stage (b) additionally a heat duty of 21 KW/($t_{MeOH}$/h), stage (c) additionally a heat duty of 50 KW/($t_{MeOH}$/h) of steam from the grid. Altogether, a heat duty of 904 KW/($t_{MeOH}$/h) is consumed. Compared to the heat consumption in example 1, the heat consumption is increased by 111%. This example clearly shows the benefit of the inventive heat integrated process.

Example 3

Heat-Integrated Process According to the Invention, Comprising Stages (a), (b), (c), (d), (x), and (y)

Propylene (chemical grade) is converted with crude hydrogen peroxide having a concentration of 40 wt.-% in the presence of methanol as solvent and TS-1 catalyst to propylene oxide in two reaction stages (i) and (iii), wherein between the two reaction stages propylene oxide is separated in a stage (ii) by distillation.

Reaction in stage (i) is performed at 20 bar, in stage (iii) at 10 bar. $H_2O_2$ conversion in stage (i) is 91%. The distillation is running at a top pressure of 1.2 bar. From the divided wall column in stage (ii) (40 theoretical stages, dividing wall from stage 8 to 32), a stream containing surplus propylene and propylene oxide is separated by distillation over the top. The side stream with a concentration of 98 wt.-% methanol and 2 wt.-% $H_2O$ is directly recycled to reaction stages (i) in an amount of 13.5% of the MeOH solvent stream applied in the process. The bottom stream containing methanol, water, unreacted hydrogen peroxide and epoxidation byproducts, e.g. glycolethers, is sent together with fresh propylene to reaction stages (iii) to convert $H_2O_2$ to 99.9%. Stream (M-a) is a mixture of the distillation top stream and the outlet stream of stage (iii) and comprises olefin oxide, unreacted olefin, methanol and water. (M-a) is sent to stage (b).

The unreacted olefin from the mixture (M-a) is separated by distillation (b) in a distillation column with 14 theoretical stages at a pressure of 1.1 bar to obtain a mixture (M-bi) at the top of the column comprising 89 wt.-% of olefin, 5.6 wt.-% of propane, 4 wt.-% methanol and 1.4 wt.-% of oxygen, and a mixture (M-bii) comprising methanol, water and 11.1 wt.-% of olefin oxide. After separation of oxygen by adsorption from stream (M-bi), propylene is separated from the resulting mixture in a stage (x) by distillation in a distillation tower with 130 theoretical stages operated at a pressure of 24.5 bar to obtain a mixture (M-x) comprising 96 wt.-% of propylene and 4 wt.-% propane. (M-x) is re-introduced into stage (a). A mixture of 88 wt.-% propane, 5 wt.-% propylene and 7 wt.-% MeOH is obtained at the bottom of the tower.

Subsequently, the crude olefin oxide is separated from the mixture (M-bii) in a distillation stage (c) at 0.5 bar in a distillation tower having 80 theoretical stages to obtain a top mixture (M-ci) comprising 99.8 wt.-% of olefin oxide, 0.04 wt.-% of propylene, 0.04 wt.-% of acetaldehyde, 0.01 wt.-% of methanol, 0.01 wt.-% of methanol and a mixture (M-cii) comprising 76.2 wt.-% of methanol, 22.7 wt.-% water; the rest being heavy boiling byproducts of the epoxidation. The pure olefin oxide (>99.9 wt.-% propylene oxide) is separated from the mixture (M-ci) by distillation at a pressure of 4 bar in a distillation tower having 45 theoretical stages as a side stream product from theoretical stage 5.

Low boiling compounds having a boiling point lower than methanol and lower than water are separated in a stage (y) from the mixture (M-cii) over the top of a distillation tower having 15 theoretical stages by distillation at a pressure of 1 bar to obtain a top stream mixture comprising 20 wt.-% lower boiling components such as acetaldehyde and propionaldehyde and 7 wt.-% water. The rest is MeOH. A bottoms stream (M-y) is obtained.

The solvent methanol is separated from the bottoms stream mixture (M-y) in two thermally coupled distillation columns. (M-y) is introduced into a first distillation column (13 theoretical stages) from which the vapor top stream (Td) is obtained, the distillation being carried out at a top pressure of 3.9 bar. The bottoms stream obtained is introduced into a second distillation column, a divided wall column (40 theoretical stages, dividing wall from stage 6 to stage 30), the distillation being carried out at a top pressure of 10.8 bar. Two thermally coupled distillation towers are realized such that the condenser used to condense the top stream obtained from the second tower is simultaneously used as vaporizer for the first column. The mixture (M-di) (liquid top product of the second column) comprises 98 wt.-% of methanol and 2 wt.-% of water, the mixture (M-dii) (bottom product of the second column) comprises 97.5 wt.-% of water, 2 wt.-% propylene glycol, 0.05 wt.-% monoglycol ethers, 0.45 wt.-% higher glycol ethers, and the mixture (M-diii) (side stream product of the second column) comprises 22 wt.-% glycol ethers and 88 wt.-% water. The second methanol/water separation column is operated with 16 bar steam (water steam) from the grid.

The MeOH-vapour top stream (Td), obtained from the first distillation column used in (d) having a pressure of 3.9 bar and a temperature of 104° C., and comprising 98 wt-% methanol and 2 wt.-% $H_2O$, is used to operate vaporizers (reboilers) used in distillation column used as mentioned in the separation stages (a), (b), (x), (c), and (y).

The following heat duties, calculated per metric ton/h recycled methanol as solvent, are needed to operate the above-described process:

A heat duty of 428 KW/($t_{MeOH}$/h) is necessary. Stage (a) consumes 37% (a heat duty of 158 KW/($t_{MeOH}$/h)), stage (b) consumes 5% (a heat duty of 21 KW/($t_{MeOH}$/h)), stage (x) consumes 6% (a heat duty of 25 KW/($t_{MeOH}$/h)), stage (c) consumes 12% (a heat duty of 50 KW/($t_{MeOH}$/h)) and stage (y) consumes 33% (a heat duty of 140 KW/($t_{MeOH}$/h)) of the MeOH-vapour top stream (Td), obtained from the first distillation column used in (d) having a pressure of 3.9 bar and a temperature of 104° C.

Example 4

Process According to the Prior Art, Comprising Stages (a), (B), (C), (d), (x), and (y) without Heat Integration Comparative Example Propylene (chemical grade) is converted with crude hydrogen peroxide having a concentration of 40 wt.-% in the presence of methanol as solvent and TS-1 catalyst to propylene oxide in two reaction stages (i) and (iii), wherein between the two reaction stages propylene oxide is separated in a stage (ii) by distillation.

Reaction in stage (i) is performed at 20 bar, in stage (iii) at 10 bar. $H_2O_2$ conversion in stage (i) is 91%. The distillation is running at a top pressure of 1.2 bar. From the divided wall column in stage (ii) (40 theoretical stages, dividing wall from stage 8 to 32), a stream containing surplus propylene and propylene oxide is separated by distillation over the top. The side stream with a concentration of 98 wt.-% methanol and 2 wt.-% $H_2O$ is directly recycled to reaction stages (i) in an amount of 13.5% of the MeOH solvent stream applied in the process. The bottom stream containing methanol, water, unreacted hydrogen peroxide and epoxidation byproducts, e.g. glycolethers, is sent together with fresh propylene to reaction stages (iii) to convert $H_2O_2$ to 99.9%. Stream (M-a) is a mixture of the distillation top stream and the outlet stream of stage (iii) and comprises olefin oxide, unreacted olefin, methanol and water. (M-a) is sent to stage (b).

The unreacted olefin from the mixture (M-a) is separated by distillation (b) in a distillation column with 14 theoretical stages at a pressure of 1.1 bar to obtain a mixture (M-bi) at the top of the column comprising 89 wt.-% of olefin, 5.6 wt.-% of propane, 4 wt.-% methanol and 1.4 wt.-% of oxygen, and a mixture (M-bii) comprising methanol, water and 11.1 wt.-% of olefin oxide. After separation of oxygen by adsorption from stream (M-bi), propylene is separated from the resulting mixture in a stage (x) by distillation in a distillation tower with 130 theoretical stages operated at a pressure of 24.5 bar to obtain a mixture (M-x) comprising 96 wt.-% of propylene and 4 wt.-% propane. (M-x) is re-introduced into stage (a). A mixture of 88 wt.-% propane, 5 wt.-% propylene and 7 wt.-% MeOH is obtained at the bottom of the tower.

Subsequently, the crude olefin oxide is separated from the mixture (M-bii) in a distillation stage (c) at 0.5 bar in a distillation tower having 80 theoretical stages to obtain a top mixture (M-ci) comprising 99.8 wt.-% of olefin oxide, 0.04 wt.-% of propylene, 0.04 wt.-% of acetaldehyde, 0.01 wt.-% of methanol, 0.01 wt.-% of methanol and a mixture (M-cii) comprising 76.2 wt.-% of methanol, 22.7 wt.-% water; the rest being heavy boiling byproducts of the epoxidation. The pure olefin oxide (>99.9 wt.-% propylene oxide) is separated from the mixture (M-ci) by distillation at a pressure of 4 bar in a distillation tower having 45 theoretical stages as a side stream product from theoretical stage 5.

Low boiling compounds having a boiling point lower than methanol and lower than water are separated in a stage (y) from the mixture (M-cii) over the top of a distillation tower having 15 theoretical stages by distillation at a pressure of 1 bar to obtain a top stream mixture comprising 20 wt.-% lower boiling components such as acetaldehyde and propionaldehyde and 7 wt.-% water. The rest is MeOH. A bottoms stream (M-y) is obtained.

The solvent methanol is separated from the bottoms stream mixture (M-y) in two thermally coupled distillation columns. (M-y) is introduced into a first distillation column (13 theoretical stages) from which the vapor top stream (Td) is obtained, the distillation being carried out at a top pressure of 3.9 bar. The bottoms stream obtained is introduced into a second distillation column, a divided wall column (40 theoretical stages, dividing wall from stage 6 to stage 30), the distillation being carried out at a top pressure of 10.8 bar. Two thermally coupled distillation towers are realized such that the condenser used to condense the top stream obtained from the second tower is simultaneously used as vaporizer for the first column. The mixture (M-di) (liquid top product of the second column) comprises 98 wt.-% of methanol and 2 wt.-% of water, the mixture (M-dii) (bottom product of the second column) comprises 97.5 wt.-% of water, 2 wt.-% propylene glycol, 0.05 wt.-% monoglycol ethers, 0.45 wt.-% higher glycol ethers, and the mixture (M-diii) (side stream product of the second column) comprises 22 wt.-% glycol ethers and 88 wt.-% water. The second methanol/water separation column is operated with 16 bar steam (water steam) from the grid.

In contrast to example 3, water steam from grid is used to operate vaporizers (reboilers) used in distillation column as mentioned in the separation stages (a), (x) (b), (c) and (y).

The following heat duties, calculated per metric ton/h recycled methanol as solvent, are needed to operate the above-described process:

A heat duty of 676 KW/($t_{MeOH}$/h) is necessary in stage (d). Stage (a) consumes additionally 37% (a heat duty of 158 KW/($t_{MeOH}$/h)), stage (b) additionally 5% (a heat duty of 21 KW/($t_{MeOH}$/h)), stage (x) additionally 6% (a heat duty of 25 KW/($t_{MeOH}$/h)), stage (c) consumes 12% (a heat duty of 50 KW/($t_{MeOH}$/h)) and stage (y) additionally 33% (a heat duty of 140 KW/($t_{MeOH}$/h))) of steam from the grid. Altogether a heat duty of 1068 KW/($t_{MeOH}$/h) is consumed.

Compared to the heat consumption in example 1 the heat consumption is increased by 150%. This example clearly shows the benefit of the inventive heat integrated process.

Example 5

Heat-Integrated Process According to the Invention, Comprising Stages (a), (b), (c), (d), (x), (y), and Further Heat Integration Methods According to the Invention Propylene (chemical grade) is converted with crude hydrogen peroxide having a concentration of 40 wt.-% in the presence of methanol as solvent and TS-1 catalyst to propylene oxide in two reaction stages (i) and (iii), wherein between the two reaction stages propylene oxide is separated in a stage (ii) by distillation.

Reaction in stage (i) is performed at 20 bar, in stage (iii) at 10 bar. $H_2O_2$ conversion in stage (1) is 91%. The distillation is running at a top pressure of 1.2 bar. From the divided wall column in stage (ii) (40 theoretical stages, dividing wall from stage 8 to 32), a stream containing surplus propylene and propylene oxide is separated by distillation over the top. The side stream with a concentration of 98 wt.-% methanol and 2 wt.-% $H_2O$ is directly recycled to reaction stages (i) in an amount of 13.5% of the MeOH solvent stream applied in the process. The bottom stream containing methanol, water, unreacted hydrogen peroxide and epoxidation byproducts, e.g. glycolethers, having a temperature of 79° C., is additionally used to heat up the feed mixture to the divided wall distillation tower in a counter current exchanger, before it is sent together with fresh propylene to reaction stages (iii) to convert $H_2O_2$ to 99.9%. Stream (M-a) is a mixture of the distillation top stream and the outlet stream of stage (iii) and comprises olefin oxide, unreacted olefin, methanol and water. (M-a) is sent to stage (b).

The unreacted olefin from the mixture (M-a) is separated by distillation (b) in a distillation column with 14 theoretical stages at a pressure of 1.1 bar to obtain a mixture (M-bi) at the top of the column comprising 89 wt.-% of olefin, 5.6 wt.-% of propane, 4 wt.-% methanol and 1.4 wt.-% of oxygen, and a mixture (M-bii) comprising methanol, water and 11.1 wt.-% of olefin oxide. After separation of oxygen by adsorption from stream (M-bi), propylene is separated from the resulting mixture in a stage (x) by distillation in a distillation tower with 130 theoretical stages operated at a pressure of 24.5 bar to obtain a mixture (M-x) comprising 96 wt.-% of propylene and 4 wt.-% propane. (M-x) is re-introduced into stage (a). A mixture of 88 wt.-% propane, 5 wt.-% propylene and 7 wt.-% MeOH is obtained at the bottom of the tower.

Subsequently, the crude olefin oxide is separated from the mixture (M-bii) in a distillation stage (c) at 0.5 bar in a distillation tower having 80 theoretical stages to obtain a top mixture (M-ci) comprising 99.8 wt.-% of olefin oxide, 0.04 wt.-% of propylene, 0.04 wt.-% of acetaldehyde, 0.01 wt.-% of methanol, 0.01 wt.-% of methanol and a mixture (M-cii) comprising 76.2 wt.-% of methanol, 22.7 wt.-% water; the rest being heavy boiling byproducts of the epoxidation. The pure olefin oxide (>99.9 wt.-% propylene oxide) is separated from the mixture (M-ci) by distillation at a pressure of 4 bar in a distillation tower having 45 theoretical stages as a side stream product from theoretical stage 5.

Low boiling compounds having a boiling point lower than methanol and lower than water are separated in a stage (y) from the mixture (M-cii) over the top of a distillation tower having 15 theoretical stages by distillation at a pressure of 1 bar to obtain a top stream mixture comprising 20 wt.-% lower boiling components such as acetaldehyde and propionaldehyde and 7 wt.-% water. The rest is MeOH. A bottoms stream (M-y) is obtained.

The solvent methanol is separated from the bottoms stream mixture (M-y) in two thermally coupled distillation columns. (M-y) is introduced into a first distillation column (13 theoretical stages) from which the vapor top stream (Td) is obtained, the distillation being carried out at a top pressure of 3.9 bar. The bottoms stream obtained is introduced into a second distillation column, a divided wall column (40 theoretical stages, dividing wall from stage 6 to stage 30), the distillation being carried out at a top pressure of 10.8 bar. Additionally the feed mixture to the divided wall distillation tower is heated up in a counter current exchanger with the bottom stream of this tower. Two thermally coupled distillation towers are realized such that the condenser used to condense the top stream obtained from the second tower is simultaneously used as vaporizer for the first column. The mixture (M-di) (liquid top product of the second column) comprises 98 wt.-% of methanol and 2 wt.-% of water, the mixture (M-dii) (bottom product of the second column) comprises 97.5 wt.-% of water, 2 wt.-% propylene glycol, 0.05 wt.-% monoglycol ethers, 0.45 wt.-% higher glycol ethers, and the mixture (M-diii) (side stream product of the second column) comprises 22 wt.-% glycol ethers and 88 wt.-% water. The second methanol/water separation column is operated with 16 bar steam (water steam) from the grid.

The MeOH-vapour top stream (Td), obtained from the first distillation column used in (d) having a pressure of 3.9 bar and a temperature of 104° C., and comprising 98 wt-% methanol and 2 wt.-% H2O is used to operate vaporizers (reboilers) used in distillation column used as mentioned in the separation stages (a), (b), (x), (c), and (y).

The following heat duties, calculated per metric ton/h recycled methanol as solvent, are needed to operate the above-described process:

A heat duty of 383 $KW/(t_{MeOH}/h)$ is necessary. Stage (a) consumes 35% (a heat duty of 135 $KW/(t_{MeOH}/h)$), stage (b) consumes 6% (a heat duty of 21 $KW/(t_{MeOH}/h)$), stage (x) consumes 6% (a heat duty of 25 $KW/(t_{MeOH}/h)$), stage (c) consumes 13% (a heat duty of 50 $KW/(t_{MeOH}/h)$) and stage (y) consumes 36% (a heat duty of 140 $KW/(t_{MeOH}/h)$) of the MeOH-vapour top stream (Td), obtained from the first distillation column used in (d) having a pressure of 3.9 bar and a temperature of 104° C.

Compared to the heat consumption in example 3 the heat consumption is additionally decreased by 9%. This example clearly shows the benefit of the further extended heat integrated process compared to the processes without heat integration.

We claim:
1. A process for epoxidizing an olefin comprising
 (a) reacting an olefin with hydrogen peroxide in the presence of methanol as solvent in at least two reaction stages to obtain a mixture (M-a) comprising olefin oxide, unreacted olefin, methanol, and water, wherein said olefin oxide is separated by distillation between said at least two reaction stages;
 (b) separating unreacted olefin from said mixture (M-a) by distillation to obtain a mixture (M-bi) comprising at least 80 weight % of olefin and a mixture (M-bii) comprising methanol, water, and at least 7 weight % of olefin oxide;
 (c) separating olefin oxide from said mixture (M-bii) in at least one distillation stage to obtain a mixture (M-ci) comprising at least 99 weight % of olefin oxide and a mixture (M-cii) comprising water and at least 55 weight % of methanol; and
 (d) separating methanol from said mixture (M-cii) in at least one distillation stage to obtain a mixture (M-di) comprising at least 85 weight % of methanol and up to 10 weight % of water and a mixture (M-dii) comprising at least 90 weight % of water;
 wherein a vapor top stream (Td) is obtained from at least one distillation column used in (d) and is used to operate at least partially at least one vaporizer used in at least one distillation column used in at least one of (a), (b) and (c), and wherein said vapor top stream (Td) comprises at least 85 weight % methanol.

2. The process of claim 1, wherein from 5 to 60 weight % of (Td) is used to operate at least partially a vaporizer used in (a), from 1 to 20 weight % of (Td) is used to operate at least partially a vaporizer used in (b), and from 1 to 50 weight % of (Td) is used to operate at least partially a vaporizer used in (c).

3. The process of claim 1, wherein said olefin is propene and said olefin oxide is propylene oxide.

4. The process of claim 3, wherein in (a) said mixture (M-a) further comprises propane; wherein in (b), unreacted propene is separated from said mixture (M-a) by distillation to obtain the mixture (M-bi) comprising unreacted propene and propane; wherein said process further comprises
(x) separating said unreacted propene from said mixture (M-bi) by distillation to obtain a mixture (M-x) comprising at least 90 weight % of propene;
and wherein said vapor top stream (Td) is used to operate at least partially at least one vaporizer used in at least one distillation column used in at least one of (a), (b), (c), and (x).

5. The process of claim 4, wherein from 5 to 60 weight % of (Td) is used to operate at least partially a vaporizer used in (a), from 1 to 20 weight % of (Td) is used to operate at least partially a vaporizer used in (b), from 1 to 50 weight % of (Id) is used to operate at least partially a vaporizer used in (c), and from 1 to 20 weight % of (Td) is used to operate at least partially a vaporizer used in (x).

6. The process of claim 3, wherein said mixture (M-cii) additionally comprises at least one compound having a boiling temperature lower than methanol and lower than water at a given pressure; wherein said process further comprises
(y) separating said at least one compound having a boiling point lower than methanol and lower than water from said mixture (M-cii) by distillation to obtain a mixture (M-y) comprising from 40 to 80 weight % of methanol and from 10 to 55 weight % of water; and
(d) separating said methanol from said mixture (M-y) in at least one distillation stage to obtain a mixture (M-di) comprising at least 85 weight % of methanol and up to 10 weight % of water and a mixture (M-dii) comprising at least 90 weight % of water,
and wherein said vapor top stream (Td) is used to operate at least partially at least one vaporizer used in at least one distillation column used in at least one of stages (a), (b), (e), and (y).

7. The process of claim 6, wherein from 5 to 60 weight % of (Td) is used to operate at least partially a vaporizer used in (a), from 1 to 20 weight % of (Td) is used to operate at least partially a vaporizer used in (b), from 1 to 50 weight % of (Td) is used to operate at least partially a vaporizer used in (c), and from 5 to 60 weight % of (Td) is used to operate at least partially a vaporizer used in (y).

8. The process of claim 3, wherein in (c), said mixture (M-cii) additionally comprises at least one compound having a boiling temperature lower than methanol and lower than water at a given pressure, said process comprising
(d) separating said methanol from said mixture (M-cii) in at least one distillation stage to obtain a mixture (M-di) comprising at least 85 weight % of methanol, up to 10 weight % of water and said at least one compound having a boiling temperature lower than methanol and lower than water and a mixture (M-dii) comprising at least 90 weight % of water; and
(z) separating said at least one compound having a boiling point lower than methanol and lower than water from said mixture (M-di) by distillation to obtain a mixture (M-z) comprising from 85 to 99.5 weight % of methanol and from 0.5 to 10 weight % of water;
and wherein said vapor top stream (Td) is used to operate at least partially at least one vaporizer used in at least one distillation column used in at least one of stages (a), (b), (c), and (z).

9. The process of claim 8 wherein from 5 to 60 weight % of (Td) is used to operate at least partially a vaporizer used in (a), from 1 to 20 weight % of (Td) is used to operate at least partially a vaporizer used in (b), from 1 to 50 weight % of (Td) is used to operate at least partially a vaporizer used in (c), and from 5 to 60 weight % of (Td) is used to operate at least partially a vaporizer used in (z).

10. The process of claim 1, wherein in (c), said olefin oxide is separated in two distillation columns; wherein from 0 to 20 weight % of (Td) is used to at least partially operate a vaporizer of the first distillation column from which a mixture comprising at least 98 weight % olefin oxide is obtained, said mixture being introduced into the second distillation column; and wherein from 1 to 30 weight % of (Td) is used to at least partially operate a vaporizer of the second distillation column from which an olefin oxide stream comprising at least 99.8 weight % olefin oxide is obtained.

11. The process of claim 1, additionally comprising
(e) evaporating said mixture (M-dii).

12. The process of claim 11, wherein from 5 to 60 weight % of (Td) is used to operate at least partially a vaporizer used in (a), from 1 to 20 weight % of (Td) is used to operate at least partially a vaporizer used in (b), from 1 to 50 weight % of (Td) is used to operate at least partially a vaporizer used in (c), and from 1 to 50 weight % of (Td) is used to operate at least partially a vaporizer used in (e).

13. The process of claim 1, wherein from 1 to 50 weight % of (Td) is used to at least partially operate at least one control heat exchanger used in the process.

14. The process of claim 1, wherein the feed of at least one distillation column used in stages (a), (b), (e), and (d) is heated with the bottom stream of said at least one distillation column.

15. The process of claim 1, wherein the top stream obtained from at least one distillation column used in stages (a), (b), and (c) is condensed in two stages, wherein in the first stage, the condenser is cooled with water having an inlet temperature of from 15 to 40° C., and in the second stage, the condenser is cooled with water having an inlet temperature of from 5 to 20° C., wherein the inlet temperature of the water used in said second stage is lower than the inlet temperature of the water used in said first stage.

16. The process of claim 15, wherein in (c), said olefin oxide is separated in two distillation columns, and wherein from 0 to 20 weight % of (Td) is used to at least partially operate a vaporizer of the first distillation column from which a mixture comprising at least 98 weight % of olefin oxide is obtained, said mixture being introduced into the second distillation column, and wherein from 1 to 30 weight % of (Td) are used to at least partially operate a vaporizer of the second distillation column from which an olefin oxide stream comprising at least 99.8 weight % olefin oxide is obtained, said olefin oxide stream comprising at least 99.8 weight % olefin oxide being condensed in two stages, wherein in the first stage, the condenser is cooled with water having an inlet temperature of from 15 to 40° C. and in the second stage, the condenser is cooled with water having an inlet temperature of from 5 to 20° C., wherein the inlet temperature of the water used in said second stage is lower than the inlet temperature of the water used in said first stage.

17. The process of claim 1, wherein in (d), said methanol is separated from said mixture (M-cii) in a two pressure distillation process, wherein distillation is carried out in a first distillation column at a top pressure which is different from the top pressure of a second distillation column and wherein the condenser used to condense the top stream of the first or second distillation column is used simultaneously as the vaporizer of the second or first distillation column.

18. The process of claim 17, wherein the top pressure of said first distillation column is from 2 to 8 bar and the top pressure of said second distillation column is from 8 to 15 bar.

19. The process of claim 1, wherein in (d),
(i) said mixture (M-cii) is introduced into a first distillation column (K1) from which the vapor top stream (Td) is obtained, wherein the distillation in (K1) is carried out at a top pressure of from 2.5 to 6 bar; and
(ii) the bottoms stream obtained from (K1) is introduced into a second distillation column (K2), the distillation in (K2) being carried out at a top pressure of from 9 to 13 bar;

wherein prior to introducing it into (K2), the bottoms stream obtained from (K1) is heated to a temperature of from 110 to 180° C. with the bottoms stream obtained from (K2), and wherein the condenser used to condense the top stream obtained from (K2) is simultaneously used as vaporizer of (K1).

20. The process of claim 19, wherein (K2) is a dividing wall column.

21. The process of claim 1, wherein the olefin separated in (b) is re-introduced into (a).

22. The process of claim 1, wherein the methanol separated in (d) is re-introduced into (a).

* * * * *